United States Patent
Satoh et al.

(10) Patent No.: US 8,867,808 B2
(45) Date of Patent: Oct. 21, 2014

(54) INFORMATION PROCESSING APPARATUS, INFORMATION PROCESSING METHOD, PROGRAM, AND STORAGE MEDIUM

(75) Inventors: Kiyohide Satoh, Kawasaki (JP); Takaaki Endo, Urayasu (JP); Ryo Ishikawa, Kawasaki (JP)

(73) Assignee: Canon Kabushiki Kaisha, Tokyo (JP)

( * ) Notice: Subject to any disclaimer, the term of this patent is extended or adjusted under 35 U.S.C. 154(b) by 170 days.

(21) Appl. No.: 13/129,228

(22) PCT Filed: Nov. 17, 2009

(86) PCT No.: PCT/JP2009/069755
§ 371 (c)(1),
(2), (4) Date: May 13, 2011

(87) PCT Pub. No.: WO2010/058854
PCT Pub. Date: May 27, 2010

(65) Prior Publication Data
US 2011/0216958 A1 Sep. 8, 2011

(30) Foreign Application Priority Data
Nov. 20, 2008 (JP) ................................. 2008-296698

(51) Int. Cl.
*G06K 9/00* (2006.01)
*G06T 7/00* (2006.01)
*A61B 5/055* (2006.01)

(52) U.S. Cl.
CPC ............... *G06T 7/0028* (2013.01); *A61B 5/055* (2013.01); *G06T 2207/30004* (2013.01); *G06T 2207/10132* (2013.01); *G06T 2207/10088* (2013.01)

USPC ............................ 382/131; 382/130; 382/128

(58) Field of Classification Search
None
See application file for complete search history.

(56) References Cited

U.S. PATENT DOCUMENTS

| | | | |
|---|---|---|---|
| 6,770,033 B1 * | 8/2004 | Fink et al. | 600/443 |
| 7,252,004 B2 * | 8/2007 | Fink et al. | 73/597 |
| 7,397,934 B2 * | 7/2008 | Bloch et al. | 382/128 |
| 8,433,114 B2 * | 4/2013 | Reisman et al. | 382/128 |
| 8,727,998 B2 * | 5/2014 | Yin et al. | 600/485 |
| 2007/0036402 A1 * | 2/2007 | Cahill et al. | 382/128 |
| 2007/0244393 A1 * | 10/2007 | Oshiki et al. | 600/463 |
| 2007/0280556 A1 * | 12/2007 | Mullick et al. | 382/294 |
| 2010/0220901 A1 * | 9/2010 | Matsumura | 382/128 |
| 2012/0133663 A1 * | 5/2012 | Tanigawa | 345/581 |

FOREIGN PATENT DOCUMENTS

| | | |
|---|---|---|
| JP | 2005-102713 A | 4/2005 |
| JP | 2005-521502 T | 7/2005 |
| JP | 2005-528974 A | 9/2005 |

(Continued)

OTHER PUBLICATIONS

Wein et al., "Automatic Registration and Fusion of Ultrasound with CT for Radiotherapy," Proc. MICCAI, 2005, vol. 2, pp. 303-311.

*Primary Examiner* — Nancy Bitar
(74) *Attorney, Agent, or Firm* — Canon USA, Inc. IP Division

(57) ABSTRACT

First elasticity information regarding elasticity of a subject in a first image and second elasticity information regarding the elasticity of the subject in a second image are acquired, and the first image and the second image are positioned with respect to each other on the basis of at least one of the first elasticity information and the second elasticity information.

19 Claims, 10 Drawing Sheets

(56) References Cited

FOREIGN PATENT DOCUMENTS

| JP | 3871747 B2 | 1/2007 |
| JP | 2007-319676 A | 12/2007 |
| JP | 2008-086400 A | 4/2008 |
| JP | 2010119654 A | 6/2010 |

* cited by examiner

INFORMATION PROCESSING APPARATUS, INFORMATION PROCESSING METHOD, PROGRAM, AND STORAGE MEDIUM

TECHNICAL FIELD

The present invention relates to a technique for positioning images captured by a plurality of image capturing apparatuses, and more particularly, to an image processing technique using elasticity information of a subject.

BACKGROUND ART

In the medical field, doctors display medical images of subjects on a monitor and interpret the displayed medical images to observe the statuses or changes over time of lesions. Apparatuses (modalities) for capturing this type of medical image include an X-ray computed tomography (X-ray CT) apparatus, a magnetic resonance imaging (MRI) apparatus, a nuclear medicine diagnosis apparatus (single-photon-emission computed tomography (SPECT) apparatus and positron emission tomography (PET) apparatus), and an ultrasound imaging (US) apparatus. Each of the above-mentioned modalities is capable of providing an image of internal tissues of a subject by measuring a physical quantity specific to the modality. Images obtained by different modalities have different characteristics. Therefore, doctors generally make diagnoses using a plurality of modalities. For example, an image of a subject is captured by each of the MRI apparatus and the ultrasound imaging apparatus, and a doctor makes a diagnosis by comprehensively considering the obtained information.

However, in the case where images of the same subject are captured using a plurality of modalities, the obtained images are based on different coordinate systems. Therefore, a certain point within the subject may be displayed at different positions on the obtained images. According to the related art, the images captured by different modalities are not presented to the doctors such that the geometric relationship therebetween is visualized. The doctors estimate the relationship on the basis of the information of the images obtained individually by the respective modalities. Thus, there is a problem that the relationship between the images obtained by different modalities cannot be easily recognized.

Accordingly, attempts have been made to develop a technique for positioning the images obtained by different modalities with respect to each other and presenting the images to the doctors such that the doctors can easily recognize the relationship between the images. In particular, attempts have been made to develop a technique for presenting an ultrasonic tomographic image captured in an interactive manner and a three-dimensional medical image obtained by another modality in association with each other. In Patent Citation 1, an application is discussed which obtains an MRI image of a subject in advance, generates an MRI tomographic image which corresponds to an ultrasonic tomographic image being obtained, and displays the MRI tomographic image next to the ultrasonic tomographic image. According to this application, the relationship between the ultrasonic tomographic image and the MRI image can be easily recognized, and the efficiency and accuracy of diagnosis can be increased. In addition, there may be a case in which information, such as the position of a certain type of tumor, which cannot be easily visualized by the ultrasound imaging apparatus can be visualized in an MRI image. In such a case, the pieces of information of the images can compensate for each other. As a result, a puncture guide, for example, can be accurately operated.

To position the ultrasonic tomographic image and a three-dimensional medical image with respect to each other, the position of a cross section corresponding to the ultrasonic tomographic image is determined. The position of the cross section corresponding to the ultrasonic tomographic image can be determined by, for example, measuring the position and orientation of an ultrasound probe using an external sensor. According to Patent Citation 1, a sensor which measures the position and orientation using a magnetic field is attached to an ultrasound probe, and the position and orientation of the ultrasound probe are measured by the sensor.

A technique for positioning the ultrasonic tomographic image and a three-dimensional medical image, which are obtained by respective modalities, by using the information of the images has also been discussed. An example of such a technique is discussed in Non Patent Citation 1. According to this example, an ultrasonic simulation image is generated on the basis of a CT image captured in advance. Then, the relationship between the ultrasonic tomographic image which is actually captured by the ultrasound imaging apparatus and the above-mentioned ultrasonic simulation image is determined on the basis of the image information. Thus, the images obtained by the respective modalities can be positioned with respect to each other.

However, in the method using the external sensor, it is necessary to assume that the subject is a rigid body and does not change shape. However, it may be difficult to satisfy the assumption that the subject is a rigid body depending on the part of the subject to be examined. For example, in the case where a mammary area is observed for a breast cancer examination, it is difficult to assume that the part to be examined, i.e. a breast, is a rigid body. In particular, in an ordinary examination flow in which an MRI image is captured while the subject is in a prone (face down) position and an ultrasonic image is captured while the subject is in a supine (face up) position, the shape of the breast greatly changes due to the influence of gravity. In addition, since the ultrasonic image is captured while a probe is pressed against the part of the subject being examined, the shape of the part being examined also changes due to the pressure applied by the probe.

In contrast, in the technique according to the related art in which the images are positioned with respect to each other on the basis of the image information, the images can be positioned in consideration of the fact that the examined part of the subject is a non-rigid body by compensating for the change in shape between the images. However, since the change in shape has a very large number of degrees of freedom, only a local solution can be obtained. Therefore, it is difficult to obtain a correct positioning result.

Patent Citation 1

Japanese Patent No. 03871747

Non Patent Citation 1

W. Wein, B. Roper, and N. Navab, "Automatic registration and fusion of ultrasound with CT for radiotherapy," Proc. MICCAI 2005, vol. 2, pp. 303-311, 2005.

DISCLOSURE OF INVENTION

In view of the above-described problems, the present invention provides a technique for improving the positioning accuracy between two different images.

An image processing apparatus according to an aspect of the present invention positions a first image and a second image with respect to each other. The image processing apparatus includes a first elasticity information acquiring unit configured to acquire first elasticity information regarding elasticity of a subject in the first image; a second elasticity information acquiring unit configured to acquire second elasticity information regarding the elasticity of the subject in the second image; and a positioning unit configured to position the first image and the second image with respect to each other on the basis of at least one of the first elasticity information and the second elasticity information.

Other features and advantages of the present invention will be apparent from the following description taken in conjunction with the accompanying drawings, in which like reference characters designate the same or similar parts throughout the figures thereof.

BRIEF DESCRIPTION OF DRAWINGS

The accompanying drawings, which are incorporated in and constitute a part of the specification, illustrate embodiments of the invention and, together with the description, serve to explain the principles of the invention.

DESCRIPTION OF EMBODIMENTS

Embodiments of the present invention will now be described in detail in accordance with the accompanying drawings. However, the illustrated embodiments are not intended to limit the scope of the invention.

First Embodiment

An image processing apparatus according to the present embodiment has a function of acquiring both an MRI image of a subject which is captured in advance and an ultrasonic tomographic image of the subject which is being obtained by an operator (an engineer or a doctor) in an interactive manner, generating an MRI tomographic image which corresponds to the ultrasonic tomographic image, and displaying the generated MRI tomographic image.

Figure 1:
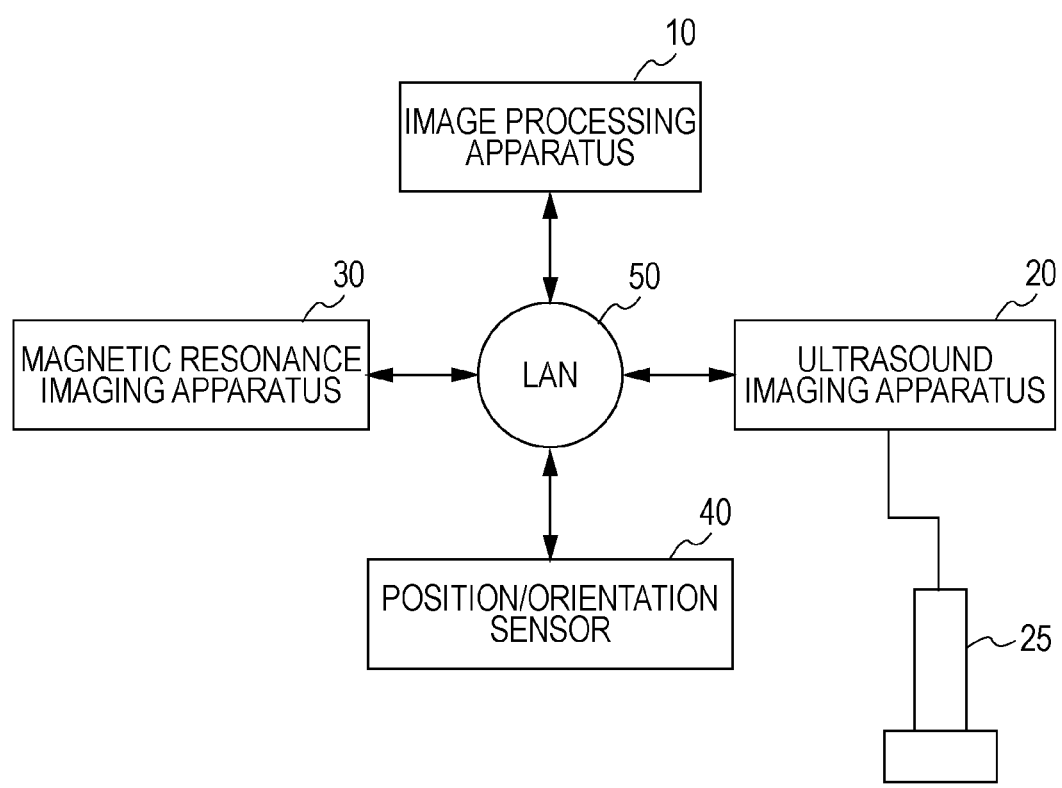
FIG. 1 is a diagram illustrating the structure of apparatuses connected to an image processing apparatus according to a first embodiment.

FIG. 1 is a diagram illustrating the structure of apparatuses connected to an image processing apparatus 10 according to the present embodiment. As shown in FIG. 1, the image processing apparatus 10 is connected to an ultrasound imaging apparatus 20, a magnetic resonance imaging apparatus 30, and a position/orientation sensor 40. These apparatuses are connected to each other via a local area network (LAN) 50 of Ethernet (trademark) or the like. The connection method is not limited to this, and the apparatuses may also be connected to each other via a universal serial bus (USB) or an interface based on IEEE 1394.

The ultrasound imaging apparatus 20 is connected to an ultrasound probe 25 including a group of ultrasound probe elements arranged in a one-dimensional array. The ultrasound imaging apparatus 20 captures a two-dimensional ultrasonic tomographic image of a subject. The ultrasonic tomographic image is obtained by bringing the ultrasound probe 25 into contact with the subject (not shown), transmitting an ultrasonic signal from the ultrasound probe 25 such that the ultrasonic signal is reflected, and receiving the reflected ultrasonic signal with the ultrasound probe 25. The ultrasound imaging apparatus 20 according to the present embodiment generates a B-mode image, which serves as a first image, and an elasticity image, which serves as first elasticity information, of the subject as the tomographic image. The elasticity image (hereinafter sometimes referred to as "ultrasonic elasticity image") represents the information regarding the elasticity of the subject for which the B-mode image is captured. The ultrasonic elasticity image can be generated by, for example, a method based on an amount of deformation of the image caused when a pressure is applied to the subject by the ultrasound probe 25 or a method using a pulsation. However, the method for generating the ultrasonic elasticity image is not particularly limited. The images generated by the ultrasound imaging apparatus 20 are transmitted to the image processing apparatus 10 through the LAN 50.

The magnetic resonance imaging apparatus 30 generates a three-dimensional image based on physical characteristics regarding magnetic resonance in an internal tissue of the subject. Thus, a three-dimensional MRI image, which serves as a second image, is obtained. The image captured by the magnetic resonance imaging apparatus 30 is, for example, a T1-weighted image. However, a T2-weighted image or an image in another mode may also be obtained as necessary, and a contrast medium may also be used. In addition, images in multiple modes may be obtained. The MRI image generated by the magnetic resonance imaging apparatus 30 is transmitted to the image processing apparatus 10 through the LAN 50.

The position/orientation sensor 40 measures the position and orientation of the ultrasound probe 25 and transmits the measurement result to the image processing apparatus 10 through the LAN 50. Any type of sensor may be used as the position/orientation sensor 40. For example, a magnetic sensor which uses a magnetic field or an optical sensor which includes a marker and a camera can be used.

Figure 2:
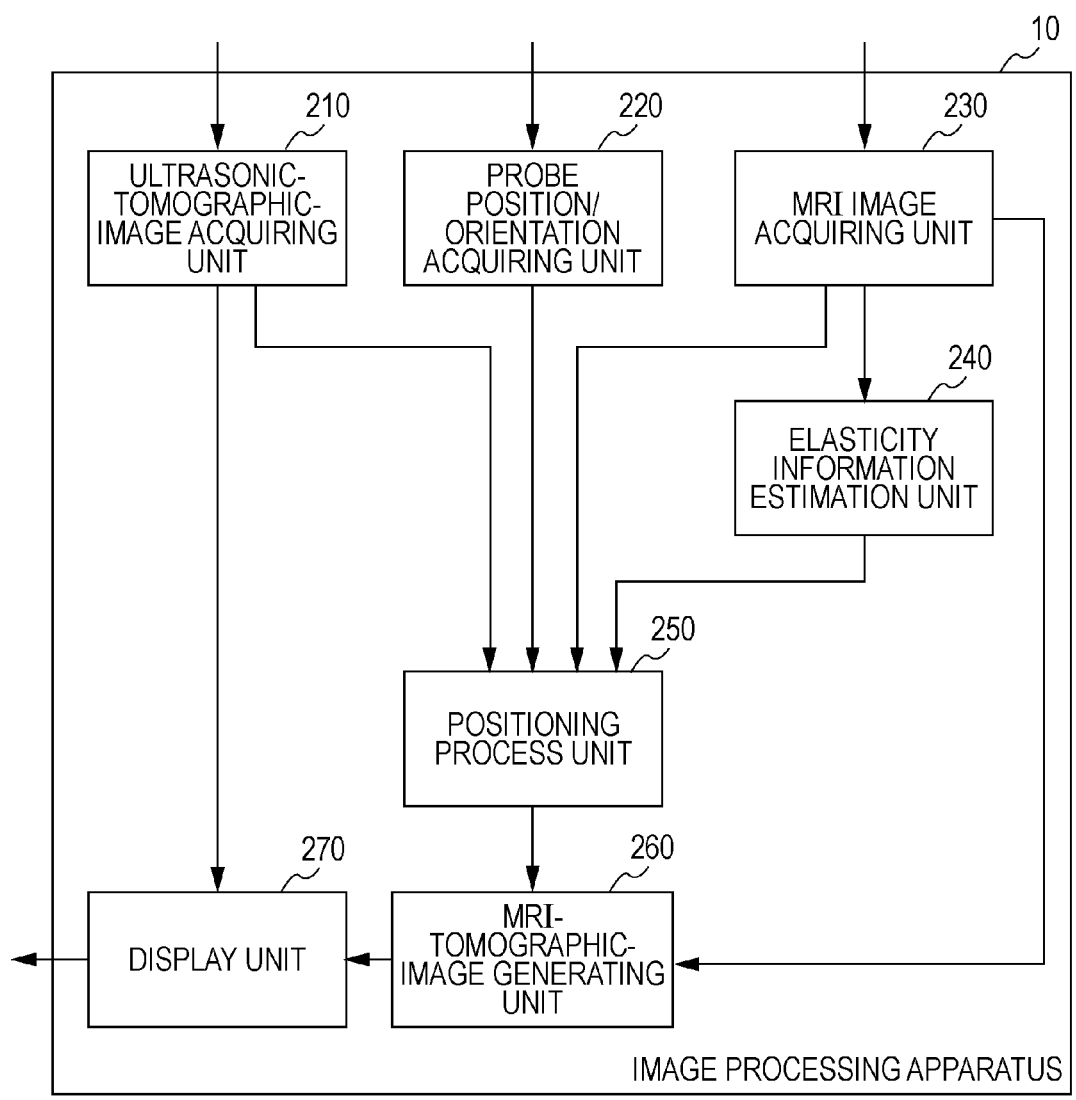
FIG. 2 is a diagram illustrating the functional structure of the image processing apparatus according to the first embodiment.

Referring to FIG. 2, the functional structure of the image processing apparatus 10 according to the present embodiment will be described. FIG. 2 is a functional block diagram of the image processing apparatus 10. As shown in FIG. 2, the image processing apparatus 10 includes an ultrasonic-tomographic-image acquiring unit 210, a probe position/orientation acquiring unit 220, an MRI image acquiring unit 230, an elasticity information estimation unit 240, a positioning process unit 250, an MRI-tomographic-image generating unit 260, and a display unit 270.

The ultrasonic-tomographic-image acquiring unit 210, which functions as a first image acquiring unit and a first elasticity-information acquiring unit, acquires an ultrasonic tomographic image (B-mode image and elasticity image) captured by the ultrasound imaging apparatus 20.

The probe position/orientation acquiring unit 220 acquires the position and orientation of the ultrasound probe 25 measured by the position/orientation sensor 40.

The MRI image acquiring unit 230, which functions as a second image acquiring unit, acquires an MRI image captured by the magnetic resonance imaging apparatus 30.

On the basis of the MRI image acquired by the MRI image acquiring unit 230, the elasticity information estimation unit 240, which functions as a second elasticity-information acquiring unit, estimates the information regarding the elasticity of the subject in the MRI image as second elasticity information. Thus, an MRI elasticity image is obtained.

The positioning process unit 250 performs a non-rigid body deformation positioning process for positioning the ultrasonic tomographic image acquired by the ultrasonic-tomographic-image acquiring unit 210 and the MRI image acquired by the MRI image acquiring unit 230 with respect to each other. In this process, deformation parameters of the MRI image and the position and orientation of the ultrasonic tomographic image in an MRI coordinate system are determined and are output to the MRI-tomographic-image generating unit 260. The process performed by the positioning process unit 250 will be described in detail below with reference to the flowchart shown in FIG. 5.

The MRI-tomographic-image generating unit 260 generates an MRI tomographic image corresponding to the ultrasonic tomographic image in accordance with the positioning result obtained by the positioning process unit 250. More specifically, an image of an area corresponding to the ultrasonic tomographic image is extracted from the MRI image captured in advance.

The display unit 270 displays the ultrasonic B-mode image obtained by the ultrasonic-tomographic-image acquiring unit 210 and the MRI tomographic image generated by the MRI-tomographic-image generating unit 260 on a monitor such that the images are arranged horizontally or vertically next to each other.

The units included in the image processing apparatus 10 shown in FIG. 2 may be provided as software which realizes the functions of the units when the software is executed by a central processing unit (CPU) of a computer. In the present embodiment, the units included in the image processing apparatus 10 are provided as software which is installed in a single computer.

Figure 3:
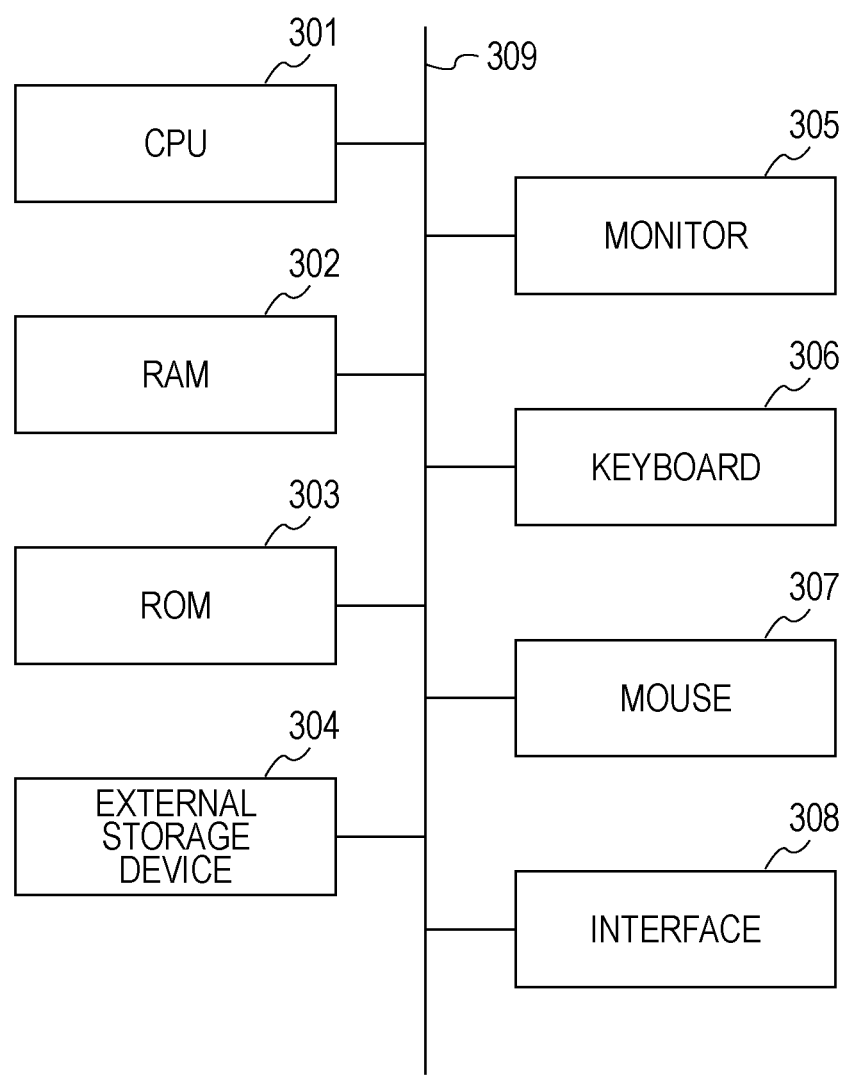
FIG. 3 is a diagram illustrating the basic structure of a computer which realizes the functions of the image processing apparatus according to the first embodiment by executing software.

FIG. 3 is a diagram illustrating the basic structure of the computer which executes the software to realize the functions of the units included in the image processing apparatus 10.

A CPU 301 controls the overall operation of the computer using programs and data stored in a random-access memory (RAM) 302 and a read-only memory (ROM) 303. The CPU 301 realizes the functions of the units included in the image processing apparatus 10 by controlling the execution of the software which corresponds to the units.

The RAM 302 has an area which temporarily stores programs and data loaded from an external storage device 304 and a work area required by the CPU 301 to perform various processes. The ROM 303 generally stores a basic input/output system (BIOS) and setting data of the computer. The external storage device 304 functions as a large-capacity information storage device, such as a hard disk drive, and stores an operating system and programs executed by the CPU 301. Information regarded as being known in the description of the present embodiment is stored in the external storage device 304, and is loaded to the RAM 302 as necessary.

A monitor 305 includes a liquid crystal display or the like. The monitor 305 can display, for example, the contents output by the display unit 270. A keyboard 306 and a mouse 307 are input devices which can be operated by an operator to input various instructions to the image processing apparatus 10.

An interface 308 is configured to communicate various data between the image processing system 10 and an external device, and includes an IEEE 1394 port, a USB port, an Ethernet (trademark) port, or the like. Data obtained through the interface 308 is stored in the RAM 302. The functions of the ultrasonic-tomographic-image acquiring unit 210, the probe position/orientation acquiring unit 220, the MRI image acquiring unit 230, etc., are realized through the interface 308.

The above-described elements are connected to each other by a bus 309.

The sequence of processes performed by the image processing apparatus 10 of the present embodiment will now be described with reference to the flowchart shown in FIG. 4. The functions of the units included in the image processing apparatus 10 according to the present embodiment are realized by causing the CPU 301 to execute the programs corresponding to the functions and controlling the overall operation of the computer. A program code corresponding to the flowchart is loaded from the external storage device 304 to the RAM 302 before the processes described below are performed.

Step S410

In step S410, the MRI image acquiring unit 230 acquires an MRI image captured by the magnetic resonance imaging apparatus 30, and transmits the MRI image to the elasticity information estimation unit 240, the positioning process unit 250, and the MRI-tomographic-image generating unit 260. The MRI image acquiring unit 230 can acquire the MRI image directly from the magnetic resonance imaging apparatus 30. Alternatively, the image captured by the magnetic resonance imaging apparatus 30 may be recorded in a medical image recording apparatus (not shown), and a desired image can be read from the medical image recording apparatus.

Step S420

In step S420, the elasticity information estimation unit 240 subjects the MRI image acquired in step S410 to image processing to estimate the information (second elasticity information) regarding the elasticity of the subject in the MRI image, thereby generating an MRI elasticity image. The generated MRI elasticity image is transmitted to the positioning process unit 250.

The process of step S420 can be performed by a method disclosed in "Biomechanical model initialized non-rigid registration for image-guided breast surgery" by T. J. Carter, C. Tanner, W. R. Crum, and D. J. Hawkes, Proc. MICCAI 2006 Workshop on Computational Biomechanics for Medicine, pp. 104-112, 2006. According to this method, the acquired MRI image is subjected to image processing for dividing the image into areas representing tissues with different elastic moduli (for example, into areas of fat, mammary gland, pectoral muscle, etc., in the case where a breast is being examined). Then, a three-dimensional image is obtained as the MRI elasticity image by substituting elasticity parameters of the tissues into the respective areas. The elasticity parameters of the tissues are stored in advance as statistical information.

Step S430

In step S430, the ultrasonic-tomographic-image acquiring unit 210 acquires an ultrasonic tomographic image (B-mode image and elasticity image) captured by the ultrasound imaging apparatus 20. The B-mode image is transmitted to the positioning process unit 250 and the display unit 270. The ultrasonic elasticity image is transmitted to the positioning process unit 250. The ultrasonic-tomographic-image acquiring unit 210 can directly acquire the ultrasonic tomographic image in synchronization with the image capturing process performed by the ultrasound imaging apparatus 20. Alternatively, tomographic images captured by the ultrasound imaging apparatus 20 in the past may be recorded in the medical image recording apparatus (not shown) and a desired tomographic image can be read from the medical image recording apparatus.

Step S440

In step S440, the probe position/orientation acquiring unit 220 acquires measured values of the position and orientation of the ultrasound probe 25 obtained by the position/orientation sensor 40. The measured values are converted into a position and an orientation of the ultrasonic tomographic image in the MRI coordinate system (the coordinate system which defines the MRI image acquired in step S410). The thus-obtained position and orientation are transmitted to the positioning process unit 250.

In the present embodiment, the relationship between the sensor coordinate system determined by the position/orientation sensor 40 and the MRI coordinate system is calibrated in advance, and a transformation therebetween is obtained by the probe position/orientation acquiring unit 220 in advance as known information. The relationship between the ultrasound probe 25 and the ultrasonic tomographic image is also calibrated in advance, and a transformation therebetween is obtained by the probe position/orientation acquiring unit 220 in advance as known information. The process of converting the position and orientation of the probe in the sensor coordinate system into the position and orientation of the ultrasonic tomographic image in the MRI coordinate system can be performed by a known method of coordinate transformation using the above-mentioned transformations, and detailed explanations thereof are thus omitted.

The posture of the subject in the MRI process differs from the posture of the subject in the image capturing process using the ultrasound probe 25. Since the subject is an elastic body, the subject is influenced by the gravity and the shape thereof is not completely constant. In addition, the position and orientation of the ultrasonic tomographic image in the MRI coordinate system obtained in step S440 include errors due to the elasticity of the subject. Therefore, if an MRI tomographic image is generated using the position and orientation obtained in step S440, it is difficult to obtain a tomographic image which completely corresponds to the ultrasonic tomographic image. An object of the positioning process performed in step S450 is to correct the images using the known information.

Step S450

In step S450, the positioning process unit 250 performs a non-rigid body deformation positioning process on the basis of the information acquired in the above-described steps. In the non-rigid body deformation positioning process, the MRI image acquired in step S410 and the B-mode image acquired in step S430 are positioned with respect to each other. More specifically, first, deformation parameters (displacements of control points set in a grid pattern in the MRI coordinate system in the present embodiment) of the MRI image and the position and orientation of the ultrasonic tomographic image in the MRI coordinate system are obtained. The thus-obtained values are output to the MRI-tomographic-image generating unit 260. The detailed process performed in step S450 will be described in detail below with reference to the flowchart shown in FIG. 5.

Step S460

In step S460, the MRI-tomographic-image generating unit 260 generates an MRI tomographic image corresponding to the ultrasonic tomographic image on the basis of the deformation parameters of the MRI image and the position and orientation of the ultrasonic tomographic image in the MRI coordinate system obtained in step S450. First, an MRI image after deformation is generated as volume data using a known interpolation method, such as B-Spline method, in accordance with the displacements of the control points. Then, the coordinates of points on the ultrasonic tomographic image in the MRI coordinate system are determined on the basis of the position and orientation of the ultrasonic tomographic image, and pixel values at the points are calculated by interpolation of pixel values of the MRI image after deformation at positions near the points. Instead of generating the MRI image after deformation as volume data, the MRI tomographic image can also be generated by calculating only the pixel values of the MRI image after deformation at the coordinates of necessary points.

It is not necessary that the image generated by the MRI-tomographic-image generating unit 260 be the exact same image as the MRI tomographic image which corresponds to the position and orientation of the ultrasonic tomographic image. For example, the MRI tomographic image may be subjected to an emphasizing process or a noise reduction process needed to display the image. Alternatively, an image obtained by integrating the pixel values of the MRI image over a certain range which is perpendicular to the cross section can also be generated. Alternatively, a maximum intensity projection (MIP) of the MRI image which corresponds to the cross section may be generated. Any kind of image can be generated as long as the image corresponds to the cross section and the image can be generated from the MRI image.

Step S470

In step S470, the display unit 270 displays the ultrasonic B-mode image acquired in step S430 and the MRI tomographic image generated in step S460 on the monitor 305 such that the images are arranged horizontally or vertically next to each other.

Step S480

In step S480, the image processing apparatus 10 determines whether or not an instruction to end the process has been input by the operator. If the instruction to end the process has been input, all of the processes are ended. If the instruction to end the process has not been input, the procedure returns to step S430. Then, the processes of steps S430 to S470 are repeated for a new ultrasonic tomographic image (the next ultrasonic tomographic image if ultrasonic tomographic images are being captured in time series). The instruction from the operator can be input through, for example, the keyboard 306.

The process of the image processing apparatus 10 is performed as described above.

The sequence of the non-rigid body deformation positioning process performed by the positioning process unit 250 in step S450 will now be described with reference to the flowchart shown in FIG. 5. In the process described below, the positioning process unit 250 estimates unknown positioning parameters $s_1$ and $s_2$. Here, $s_1$ represents the estimated values of the position and orientation of the ultrasonic tomographic image in the MRI coordinate system. For example, $s_1$ includes values showing the position in three degrees of freedom and values (Euler angles or quaternion parameters) showing the orientation in three degrees of freedom. On the other hand, $s_2$ shows the estimated values of deformation parameters of the MRI tomographic image. In the present embodiment, the deformation parameters are defined as displacements of the control points set in a grid pattern in the MRI coordinate system.

Step S505

In step S505, the positioning process unit 250 estimates the deformation parameters of the MRI image based on the gravity on the basis of the MRI elasticity image generated in step S420.

In the present embodiment, there may be a case in which the posture of the subject in the MRI process differs from the posture of the subject in the ultrasound imaging process. Therefore, in the positioning process, it may be effective to take into consideration the deformation of the subject due to the difference in the direction of gravity. Accordingly, first, a virtual MRI image of the subject in the posture for the ultrasound imaging process is obtained by deforming the MRI image obtained in step S410. Deformation parameters used in this process are estimated from the information regarding the direction of gravity and the elasticity information of the MRI image. For example, deformation parameters (displacements of control points) based on the gravity are estimated by simulation using a known finite element method (see Non Patent Literature 2). More specifically, the MRI image is deformed using the elasticity information of the subject obtained in step S420 in consideration of the gravity applied to the subject if the subject is in the posture for the ultrasound imaging process. Similarly, the image obtained by the ultrasound imaging process can also be deformed.

Step S510

In step S510, the positioning process unit 250 sets the unknown positioning parameters to initial values. To be more specific, the measured values of the position and orientation of the ultrasonic tomographic image in the MRI coordinate system obtained in step S440 are set as the initial values of s1. In addition, the deformation parameters based on the gravity obtained in step S505 are set as the initial values of $s_2$.

Step S515

In step S515, the positioning process unit 250 evaluates the positioning consistency based on the initial values set in step S510. The positioning consistency between the MRI image deformed on the basis of the deformation parameters $s_2$ and the ultrasonic tomographic image positioned at $s_1$ is evaluated, and an evaluation value is calculated.

The evaluation of the positioning consistency is performed in consideration of not only the consistency between the MRI image and the ultrasonic tomographic image but also the consistency between the MRI elasticity image and the ultrasonic elasticity image. The elasticity information is specific to the subject irrespective of the modality. Therefore, the accuracy of the consistency evaluation can be improved. If the positioning process is performed using only the MRI image and the ultrasonic tomographic image, there is a possibility that the values will converge on local solutions. If the elasticity information is additionally used, the values can be caused to converge on true values.

In the present embodiment, an evaluation value e of the consistency is calculated by the following equation.

$$e(F_{US}, F_{MRI}, I_{US}, I_{MRI}, s_1, s_2) = \alpha \cdot e_F(F_{US}, F_{MRI}, s_1, s_2) + (1-\alpha) \cdot e_I(I_{US}, I_{MRI}, s_1, s_2) \quad (1)$$

In the above equation, $F_{US}$, $F_{MRI}$, $I_{US}$, and $I_{MRI}$ show the ultrasonic elasticity image, the MRI elasticity image, the ultrasonic tomographic image, and the MRI image, respectively. In addition, $e_F$ shows the evaluation value of the consistency between the ultrasonic elasticity image and the MRI elasticity image obtained when the parameters are $s_1$ and $s_2$, and $e_I$ shows the evaluation value of the consistency between the ultrasonic tomographic image and the MRI image obtained when the parameters are $s_1$ and $s_2$. In addition, $\alpha$ is a parameter that shows the blend ratio between $e_F$ and $e_I$, and is set to a value between 0 and 1. The positioning process unit 250 changes the value of $\alpha$ in accordance with the elasticity information of the subject. A plurality of elasticity ranges are set in advance, and the value of $\alpha$ is changed in accordance with an elasticity range to which the elasticity of the subject belongs. Thus, the value of $\alpha$ is adaptively determined in accordance with the examined part of the subject. For example, in the case where the examined part is, for example, a breast and is made of a soft tissue, the elasticity is in a high-elasticity range and the value of $\alpha$ is increased. In the case where the examined part is a hand, a foot, etc., which is mainly made of an osseous part, the elasticity is in a low-elasticity range and therefore the value of $\alpha$ is reduced. The value of $\alpha$ can also be changed in accordance with the statistics, such as the average, the intermediate value, the mode, etc., of the elasticity information of the subject. Thus, in the case where the deformation due to the elasticity is large, the ratio of the evaluation value which shows the consistency between the ultrasonic elasticity image and the MRI elasticity image can be increased. The positioning process unit 250 can also change the value of $\alpha$ in accordance with the postures of the subject in the ultrasonic elasticity image and the MRI elasticity image. The value of $\alpha$ is reduced if the postures of the subject in the processes of obtaining the respective images are close to each other, and is increased if the postures of the subject are different from each other. The positioning process unit 250 digitalizes the correlation between the postures of the subject in the processes of obtaining the respective images by a numerical value, and changes the value of $\alpha$ in accordance with the numerical value. For example, the postures of the subject can be digitalized by angles between the horizontal and vertical directions, and the value of $\alpha$ may be changed in accordance with the angles of the subject in the respective images and the difference between the angles of the subject in the respective images.

The value of $\alpha$ can also be set to a fixed value in advance. Alternatively, the value of $\alpha$ can be set by the operator of the image processing apparatus 10 as necessary.

The evaluation value $e_F$ between the ultrasonic elasticity image and the MRI elasticity image is calculated by the following equation.

$$e_F(F_{MRI}, F_{US}, s_1, s_2) = e'_F(F'_{MRI}, F'_{US}) \quad (2)$$

In the above equation, $F'_{MRI}$ shows a tomographic image extracted from the MRI elasticity image as across section corresponding to the cross section of the ultrasonic tomographic image on the assumption that the positioning parameters are $s_1$ and $s_2$. The tomographic image can be generated by a process similar to that performed in step S460. In addition, $e'_F$ is an evaluation value showing the consistency between the ultrasonic elasticity image and the tomographic image extracted from the MRI elasticity image. The calculation of $e'_F$ is performed on the basis of the mean-square-error criterion by the following equation.

$$e'_F(F_{US}, F'_{MRI}) = C_{SSD}(F_{US}, F'_{MRI}) \quad (3)$$

$$= \frac{1}{M} \sum_{x_i \in \Omega} (F_{US}(x_i) - F'_{MRI}(x_i))^2$$

In the above equation, $\Omega$ shows the coordinates of each point in the ultrasonic elasticity image, and M shows the number of added pixels. The method for calculating $e'_F$ is not limited to this. For example, other known evaluation criteria, such as an absolute error criterion, a cross-correlation criterion, a mutual information criterion, a normalized mutual information criterion, etc., for evaluating the consistency or the similarity between the images may also be used. Alternatively, the consistency may also be evaluated after obtaining feature values, such as inclinations, from the images. Thus, the evaluation value may be calculated by various methods. In addition, another criterion that is similar to any one of the above-described criteria may be used, or the above-mentioned criteria may be used in combination by calculating a weighted sum.

The evaluation value $e_I$ between the ultrasonic tomographic image and the MRI image is calculated by the following equation.

$$e_I(I_{MRI}, I_{US}, s_1, s_2) = e'_I(I'_{MRI}, I_{US}) \quad (4)$$

In the above equation, $I'_{MRI}$ shows a tomographic image extracted from the MRI image as a cross section corresponding to the cross section of the ultrasonic tomographic image on the assumption that the positioning parameters are $s_1$ and $s_2$. The tomographic image can be generated by a process similar to that performed in step S460. In addition, $e'_I$ is an evaluation value showing the consistency between the ultrasonic elasticity image and the tomographic image extracted from the MRI image. The calculation of $e'_I$ can be performed by a method similar to the method for calculating $e'_F$. Therefore, detailed explanations thereof are omitted.

Step S520

In step S520, the positioning process unit 250 determines whether or not the evaluation value of the positioning consistency calculated in step S515 is sufficiently high. If the evaluation value is higher than a predetermined threshold, it is determined that the positioning is sufficiently accurate and the procedure proceeds to step S560. If the evaluation value is equal to or less than the predetermined threshold, the procedure proceeds to step S525 and the positioning process is continued.

In the following steps, the positioning process is continued by alternately estimating the parameters $s_1$ and $s_2$. First, in steps S525 to S535, the estimated values $s_1$ of the position and orientation of the ultrasonic tomographic image are corrected to perform rigid-body positioning between the MRI image after the deformation and the ultrasonic tomographic image.

Step S525

In step S525, the positioning process unit 250 generates some hypotheses about the position and orientation by adding small different changes to the current estimated values $s_1$ of the position and orientation of the ultrasonic tomographic image. Then, for each of the hypotheses about the position and orientation, the positioning consistency between the MRI image deformed on the basis of the deformation parameters $s_2$ (regarded as being fixed in this step) and the ultrasonic tomographic image is evaluated, and an evaluation value is calculated. The evaluation value of the positioning consistency is calculated for each hypothesis by a method similar to that used in step S515.

Step S530

In step S530, the positioning process unit 250 selects the highest evaluation value obtained in step S525. Then, the position and orientation of the hypothesis for which the highest evaluation value is obtained (that is, the best hypothesis) are set as the new estimated values $s_1$ of the position and orientation of the ultrasonic tomographic image. However, if the highest evaluation value is lower than the evaluation value obtained by the current estimated values, the estimated values are not updated.

Step S535

In step S535, the positioning process unit 250 determines whether or not the estimated values of the position and orientation of the ultrasonic tomographic image have converged. If it is determined that the estimated values have not yet converged, the procedure proceeds to step S525 and the process of generating some hypotheses and selecting the best hypothesis is repeated. If it is determined that the estimated values have converged, the procedure proceeds to step S540. It is determined that the estimated values have converged if, for example, the amount of improvement in the evaluation value obtained in step S530 is equal to or less than a predetermined threshold. Alternatively, it may be determined that the estimated values have converged when a difference between the new estimated values and the old estimated values is equal to or less than a predetermined threshold. The determination may also be performed by other methods. Alternatively, the number of times the above-described process has been repeated may be counted, and it may be determined to stop repeating the process when the number of times reaches a predetermined number. In such a case, it can be expected that the repeated calculations will end within a certain time period, and the real time requirement of the entire system can be met.

Next, in steps S540 to S550, the deformation parameters $s_2$ (displacements of the control points) of the MRI image are corrected to perform non-rigid-body positioning between the MRI image after the deformation and the ultrasonic tomographic image.

Step S540

In step S540, the positioning process unit 250 generates some hypotheses about the deformation parameters by adding small different changes to the estimated values $s_2$ of the deformation parameters. Then, for each hypothesis, the positioning consistency between the MRI image deformed on the basis of the hypothesis and the ultrasonic tomographic image positioned at $s_1$ (regarded as being fixed in this step) is evaluated, and an evaluation value is calculated. The evaluation value of the positioning consistency is calculated for each hypothesis by a method similar to that used in step S515.

The hypotheses can be generated by calculating the positioning consistency for each of local areas near the control points in the step of evaluating the consistency for the current parameters, and then changing the displacements of the control points in accordance with the determined consistencies. More specifically, if the positioning consistency is ensured (the evaluation value is high) in a certain local area, the displacement of the control point which affects that local area is considered to be correct. Accordingly, small changes are added to only the displacements of the control points which are to be corrected. Alternatively, the amounts of small changes added to the displacements of the control points can be adjusted in accordance with the evaluation values. In such a case, combinational explosion of the hypotheses can be prevented and the process speed can be increased.

The range of the small changes added to the displacements of control points, that is, the deformation parameters, can be adjusted in accordance with the value of the MRI elasticity image in areas near the control points. More specifically, the range in which each control point can be displaced can be increased if is high in the elasticity in an area near the control point, and the range in which each control point can be displaced can be reduced if the elasticity is low in an area near the control point.

Step S545

In step S545, the positioning process unit 250 selects the highest evaluation value obtained in step S540. Then, the deformation parameters of the hypothesis for which the highest evaluation value is obtained (that is, the best hypothesis) are set as the new estimated values $s_2$ of the deformation parameters. However, if the highest evaluation value is lower than the evaluation value obtained by the current estimated values, the estimated values are not updated.

Step S550

Instep S550, the positioning process unit 250 determines whether or not the estimated values of the deformation parameters have converged. If it is determined that the estimated values have not yet converged, the procedure proceeds to step S540 and the process of generating some hypotheses and selecting the best hypothesis is repeated. If it is determined that the estimated values have converged, the procedure proceeds to step S555. It is determined that the estimated values have converged if, for example, the amount of improvement in the evaluation value obtained in step S545 is equal to or less than a predetermined threshold. Alternatively, it may be determined that the estimated values have converged when a difference between the new deformation parameters and the old deformation parameters is equal to or less than a predetermined threshold. The determination may also be performed by other methods. Alternatively, the number of times the above-described process has been repeated may be counted, and it may be determined to stop repeating the process when the number of times reaches a predetermined number. In such a case, it can be expected that the repeated calculations will end within a certain time period, and the real time requirement of the entire system can be met.

Step S555

Instep S555, the positioning process unit 250 determines whether or not to repeat the above-described steps. In the case where the above-described steps are to be repeated, the procedure returns to step S525 and the current parameters are further updated. If it is not necessary to repeat the above-described steps, the procedure proceeds to step S560. The determination can be performed by, for example, setting the maximum number of repetitions in advance and determining whether or not the number of repetitions of steps S525 to S550 has reached the maximum number. At this time, if the evaluation value of the positioning consistency is sufficiently high, the repetition can be stopped irrespective of the current number of repetitions. Alternatively, the repetition can also be continued until the state in which the estimation values are not updated in either of steps S530 and S545 is obtained.

Step S560

In step S560, the positioning process unit 250 outputs the deformation parameters $s_2$ of the MRI image and the position and orientation $s_1$ of the ultrasonic tomographic image obtained in the above-described steps to the MRI-tomographic-image generating unit 260 as the positioning result.

The non-rigid body deformation positioning process is performed in step S450 as described above.

By performing the above-described processes, the image processing apparatus 10 according to the present embodiment can perform high-accuracy positioning between the MRI image and the ultrasonic tomographic image by taking into consideration the consistency between the pieces of elasticity information obtained by different modalities in the process of estimating the positioning parameters.

Second Embodiment

An image processing apparatus according to the present embodiment provides a function of acquiring both an MRI image of a subject and a three-dimensional ultrasonic image of the subject and displaying the images such that the images are positioned with respect to each other.

The image processing apparatus according to the present embodiment includes a second elasticity-information acquiring unit that differs from that of the first embodiment. In the first embodiment, a tissue structure is estimated from the MRI image, and the elasticity information of the MRI image is estimated from the statistics. In contrast, in the present embodiment, the elasticity information of the subject in the MRI image is estimated using MRI images obtained while the subject is in different postures. In this case, the elasticity information based on the actual deformation of the subject can be obtained. Therefore, the accuracy of the elasticity information can be increased.

In the first embodiment, the ultrasound imaging apparatus 20, which is connected to the ultrasound probe 25 including a group of ultrasound probe elements arranged in a one-dimensional array and which obtains a two-dimensional ultrasonic tomographic image, is used as a first modality. In contrast, in the present embodiment, an ultrasound imaging apparatus 20 which is connected to an ultrasound probe 25 including a group of ultrasound probe elements arranged in a two-dimensional array and which obtains a three-dimensional ultrasonic tomographic image, is used as a first modality. Accordingly, the amount of information used in the positioning process is increased. Therefore, the obscurity of the positioning process can be reduced and the accuracy of the positioning process can be increased.

The structure of apparatuses connected to an image processing apparatus 600 according to the present embodiment is similar to that shown in FIG. 1. Similar to the image processing apparatus 10 according to the first embodiment, the image processing apparatus 600 is connected to the ultrasound imaging apparatus 20, a magnetic resonance imaging apparatus 30, and a position/orientation sensor 40 via a LAN 50.

The ultrasound imaging apparatus 20 is connected to an ultrasound probe 25 including a group of ultrasound probe elements arranged in a two-dimensional array. The ultrasound imaging apparatus 20 captures a three-dimensional ultrasonic tomographic image (B-mode image and ultrasonic elasticity image) of a subject. The image generated by the ultrasound imaging apparatus 20 is transmitted to the image processing apparatus 600 through the LAN 50.

Similar to the first embodiment, the magnetic resonance imaging apparatus 30 captures an MRI image of the subject. However, different from the first embodiment, in the present embodiment, a plurality of MRI images are captured while the subject is in different postures (in the supine position and the prone position in the following explanations). The MRI images captured while the subject is in the respective postures are transmitted to the image processing apparatus 600 through the LAN 50.

Similar to the first embodiment, the position/orientation sensor 40 measures the position and orientation of the ultrasound probe 25 and transmits the measurement result to the image processing apparatus 600 through the LAN 50.

Figure 6:
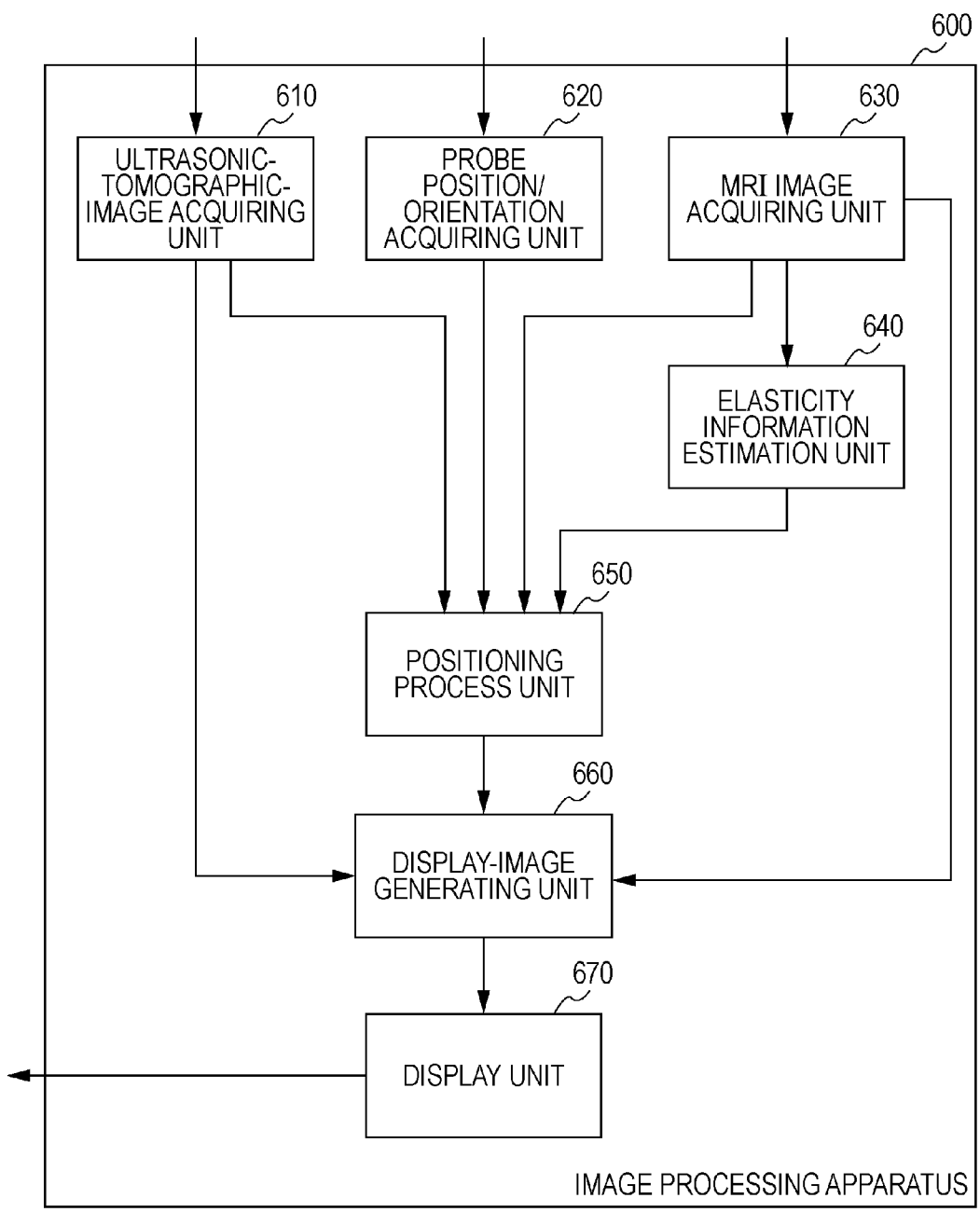
FIG. 6 is a diagram illustrating the functional structure of an image processing apparatus according to a second embodiment.

FIG. 6 is a functional block diagram of the image processing apparatus 600. As shown in FIG. 6, the image processing apparatus 600 includes an ultrasonic-image acquiring unit 610, a probe position/orientation acquiring unit 620, an MRI image acquiring unit 630, an elasticity information estimation unit 640, a positioning process unit 650, a display-image generating unit 660, and a display unit 670.

The ultrasonic-image acquiring unit 610 acquires a three-dimensional ultrasonic image (B-mode image and elasticity image) captured by the ultrasound imaging apparatus 20.

The probe position/orientation acquiring unit 620 acquires the position and orientation of the ultrasound probe 25 measured by the position/orientation sensor 40.

The MRI image acquiring unit 630 acquires a plurality of MRI images captured by the magnetic resonance imaging apparatus 30 while the subject is in different postures.

On basis of the plurality of MRI images acquired by the MRI image acquiring unit 630, the elasticity information estimation unit 640 estimates information (second elasticity information) regarding the elasticity of the subject based on one of the MRI images (the MRI image of the subject in the prone position in the following explanations). Thus, an MRI elasticity image is obtained.

The positioning process unit 650 performs a non-rigid body deformation positioning process for positioning the ultrasonic image acquired by the ultrasonic-image acquiring unit 610 and one of the MRI images (the MRI image of the subject in the prone position in the following explanations) acquired by the MRI image acquiring unit 630 with respect to each other. In this process, deformation parameters of the MRI image of the subject in the prone position and the position and orientation of the ultrasonic image in an MRI coordinate system are determined and are output to the display-image generating unit 660.

The display-image generating unit 660 generates display images in accordance with the positioning result obtained by the positioning process unit 650. The display unit 670 displays the display images generated by the display-image generating unit 660 on a monitor.

The units included in the image processing apparatus 600 shown in FIG. 6 may be provided as software which realizes the functions of the units when the software is executed by a CPU of a computer. In the present embodiment, the units included in the image processing apparatus 600 are provided as software which is installed in a single computer. The basic structure of the computer which executes the software to realize the functions of the units included in the image processing apparatus 600 is similar to that shown in FIG. 3, and explanations thereof are thus omitted.

Figure 7:
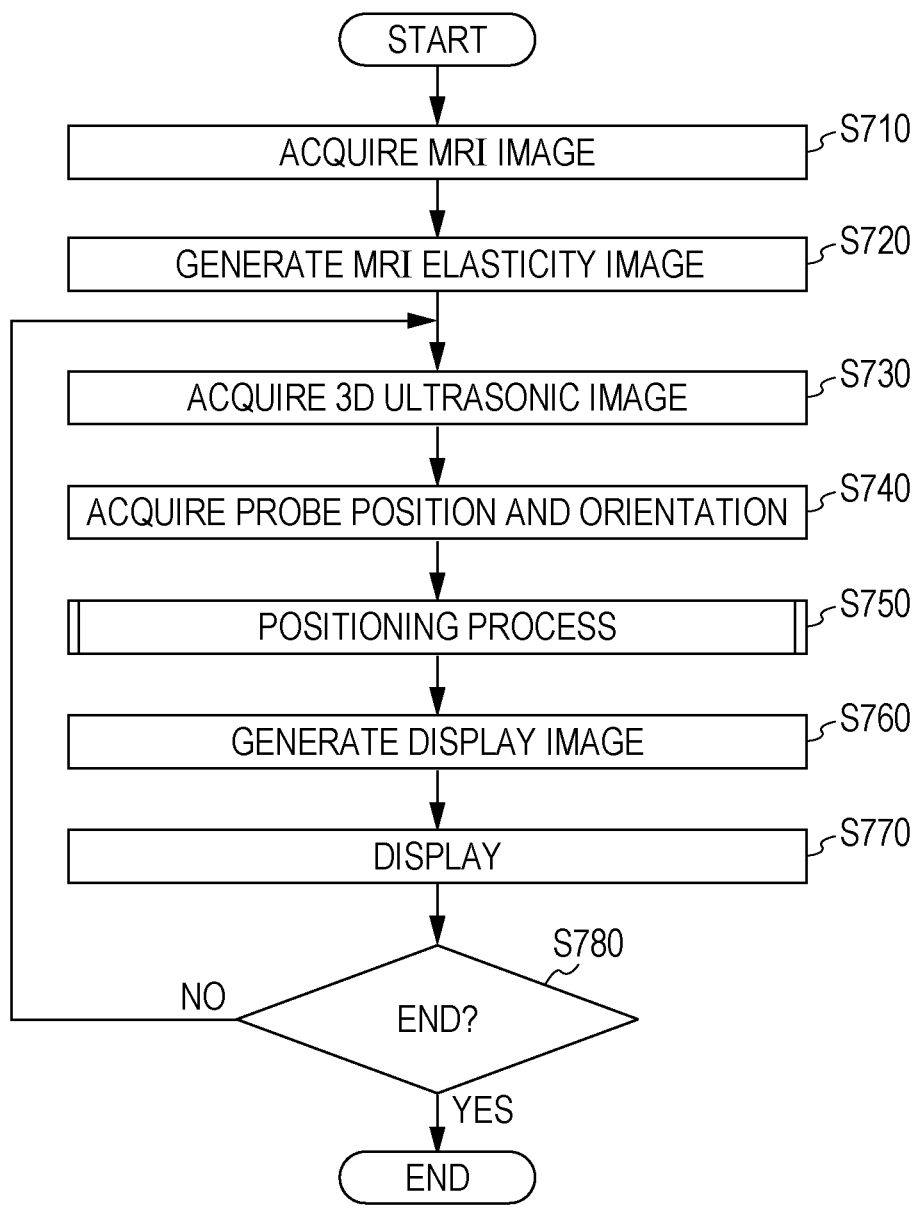
FIG. 7 is a flowchart of a process sequence performed by the image processing apparatus according to the second embodiment.

The sequence of processes performed by the image processing apparatus 600 of the present embodiment will now be described with reference to the flowchart shown in FIG. 7. The functions of the units included in the image processing apparatus 600 according to the present embodiment are realized by causing the CPU 301 to execute the programs corresponding to the functions and controlling the overall operation of the computer. A program code corresponding to the flowchart is loaded from the external storage device 304 to the RAM 302 before the processes described below are performed.

Step S710

In step S710, the MRI image acquiring unit 630 acquires a plurality of MRI images captured by the magnetic resonance imaging apparatus 30. The acquired MRI images are transmitted to the elasticity information estimation unit 640, the positioning process unit 650, and the display-image generating unit 660. The MRI image acquiring unit 630 can acquire the MRI images directly from the magnetic resonance imaging apparatus 30. Alternatively, the images captured by the magnetic resonance imaging apparatus 30 may be recorded in a medical image recording apparatus (not shown), and desired images can be read from the medical image recording apparatus.

Step S720

In step S720, the elasticity information estimation unit 640 performs a process of positioning the MRI images corresponding to a plurality of postures (the supine position and the prone position in this example) obtained in step S710. Then, on the basis of the positioning result, the information regarding the elasticity of the subject based on one of the MRI images (the MRI image of the subject in the prone position in this example) is estimated to generate an MRI elasticity image. The generated MRI elasticity image is transmitted to the positioning process unit 650.

More specifically, first, the non-rigid body deformation positioning process for positioning the MRI image of the subject in the prone position and the MRI image of the subject in the supine position with respect to each other is performed using a known method based on the similarity in brightness information. For example, points between pixels can be set in a grid pattern in the MRI image of the subject in the prone position, and then positions of the corresponding points on the MRI image of the subject in the supine position are estimated using the similarity in brightness information. This process can be performed using a free form deformation (FFD) method described in "Free-form deformation of solid geometric models" by T. W. Sederberg, Proc. SIGGRAPH '86, vol. 20, no. 4, pp. 151-160, 1986. Then, for the pixels which correspond to each other, the average of the distances to nearby control points is calculated, and the thus-obtained value is defined as a numerical value which shows the elasticity at that point. This numerical value is the elastic modulus, which increases as the softness increases. Then, the MRI elasticity image is generated by calculating elastic moduli at coordinates other than the corresponding pixel points by interpolation. In this step, the images subjected to the positioning process are obtained by the same modality. Therefore, a relatively accurate positioning result can be obtained even when only the brightness information is used.

Step S730

In step S730, the ultrasonic-image acquiring unit 610 acquires a three-dimensional ultrasonic image (B-mode image and elasticity image) captured by the ultrasound imaging apparatus 20. The B-mode image is transmitted to the positioning process unit 650 and the display-image generating unit 660. The ultrasonic elasticity image is transmitted to the positioning process unit 650. The ultrasonic-image acquiring unit 610 can directly acquire the three-dimensional ultrasonic image in synchronization with the image capturing process performed by the ultrasound imaging apparatus 20. Alternatively, images captured by the ultrasound imaging apparatus 20 in the past may be recorded in the medical image recording apparatus (not shown) and a desired image can be read from the medical image recording apparatus.

Step S740

In step S740, similar to step S440 in the first embodiment, the probe position/orientation acquiring unit 620 acquires measured values of the position and orientation of the ultrasound probe 25 obtained by the position/orientation sensor 40. The measured values are converted into a position and an orientation of the three-dimensional ultrasonic image in the MRI coordinate system (the coordinate system which defines the MRI image of the subject in the prone position acquired in step S710). The thus-obtained position and orientation are transmitted to the positioning process unit 650.

Step S750

In step S750, the positioning process unit 650 subjects one of the MRI images (the MRI image of the subject in the prone position in this example) to the non-rigid body deformation positioning process for positioning the MRI image with respect to the three-dimensional ultrasonic image acquired in step S730. More specifically, first, deformation parameters (displacements of control points set in a grid pattern in the MRI coordinate system in the present embodiment) of the MRI image of the subject in the prone position and the position and orientation of the three-dimensional ultrasonic image in the MRI coordinate system are obtained. The thus-obtained values are output to the display-image generating unit 660.

The positioning process performed in step S750 can be performed in a manner similar to that in the process of step S450 according to first embodiment. The details of this process are shown in the flowchart in FIG. 5. However, since the ultrasonic image is obtained as three-dimensional data, the method for calculating the evaluation values of consistency in steps S515, S525, and S540 differs from that in the first embodiment. More specifically, $\Omega$, which shows the points on the elasticity image in Equation (3), is expanded from a two-dimensional plane to a three-dimensional space.

In the first embodiment, the initial values of the deformation parameters $s_2$ are determined using the MRI elasticity image (step S505). However, in the present embodiment, the process of step S505 can be omitted, and deformation parameters from the prone position to the supine position can be determined from the result of the positioning process performed in step S720, and the thus-obtained deformation parameters can be used as the initial values of $s_2$. Accordingly, if, for example, the posture of the subject in the process of capturing the MRI image of the subject in the supine position is close to the posture of the subject in the process of capturing the ultrasonic image, the accuracy of the initial values can be increased.

Step S760

In step S760, the display-image generating unit 660 generates display images on the basis of the deformation parameters of the MRI image and the position and orientation of the three-dimensional ultrasonic image in the MRI coordinate system obtained in step S750. The display images include three cross-sectional images of the three-dimensional ultrasonic image based on the coordinate system of the ultrasonic image and three cross-sectional images of the MRI image corresponding to the three cross-sectional images of the three-dimensional ultrasonic image. To obtain the three cross-sectional images of the MRI image, first, the MRI image of the subject in the prone position is deformed in accordance with the displacements of the control points. Then, on the basis of the position and orientation of the three-dimensional ultrasonic image, cross sections are extracted from of the MRI image after the deformation such that the extracted cross sections correspond to the cross sections of the ultrasonic image. The display images are not limited to the three cross-sectional images of each of the three-dimensional ultrasonic image and the MRI image, and may also include, for example, an MIP image of each of the images. The apparatus may also be structured such that display mode can be selected by a user interface through, for example, the keyboard 306.

Step S770

In step S770, the display unit 670 displays the display images generated in step S760 on the monitor 305 such that the images are arranged next to each other.

Step S780

In step S780, the image processing apparatus 600 determines whether or not an instruction to end the process has been input by the operator. If the instruction to end the process has been input, all of the processes are ended. If the instruction to end the process has not been input, the procedure returns to step S730. Then, the processes of steps S730 to S770 are repeated for a new three-dimensional ultrasonic image (the three-dimensional ultrasonic image of the next frame if three-dimensional ultrasonic images are being captured in time series). The instruction from the operator can be input through, for example, the keyboard 306.

The processes of the image processing apparatus 600 are performed as described above.

In the present embodiment, the positioning process is performed by deforming the MRI image. However, in the case where both of the images obtained by different modalities are three-dimensional, either of the images obtained by the respective modalities can be deformed in the positioning process.

In the present embodiment, the three-dimensional ultrasonic image is obtained using an ultrasound probe having probe elements arranged in a two-dimensional array. However, the method for obtaining the three-dimensional ultrasonic image is not limited to this. For example, the three-dimensional ultrasonic image may also be obtained using an ultrasound probe having probe elements arranged in a one-dimensional array by combining two-dimensional ultrasonic images obtained at different positions. It is not necessary that the three-dimensional ultrasonic image data be dense, and positioning between a group of ultrasonic tomographic images obtained at discrete positions and the MRI image can also be performed. In such a case, the group of ultrasonic tomographic images obtained at different positions is regarded as a sparse three-dimensional ultrasonic image, and points on the group of ultrasonic tomographic images are defined as Ω in the process performed in step S750.

Third Embodiment

An image processing apparatus according to the present embodiment has a function of acquiring both an MRI image of a subject which is captured in advance and an ultrasonic tomographic image of the subject which is being obtained by an operator (an engineer or a doctor) in an interactive manner, generating an MRI tomographic image which corresponds to the ultrasonic tomographic image, and displaying the generated MRI tomographic image.

The structure of apparatuses connected to an image processing apparatus 800 according to the present embodiment is similar to that shown in FIG. 1. Similar to the image processing apparatus 10 according to the first embodiment, the image processing apparatus 800 is connected to the ultrasound imaging apparatus 20, a magnetic resonance imaging apparatus 30, and a position/orientation sensor 40 via a LAN 50. These apparatuses are similar to those described in the first embodiment, and explanations thereof are thus omitted.

Figure 8:
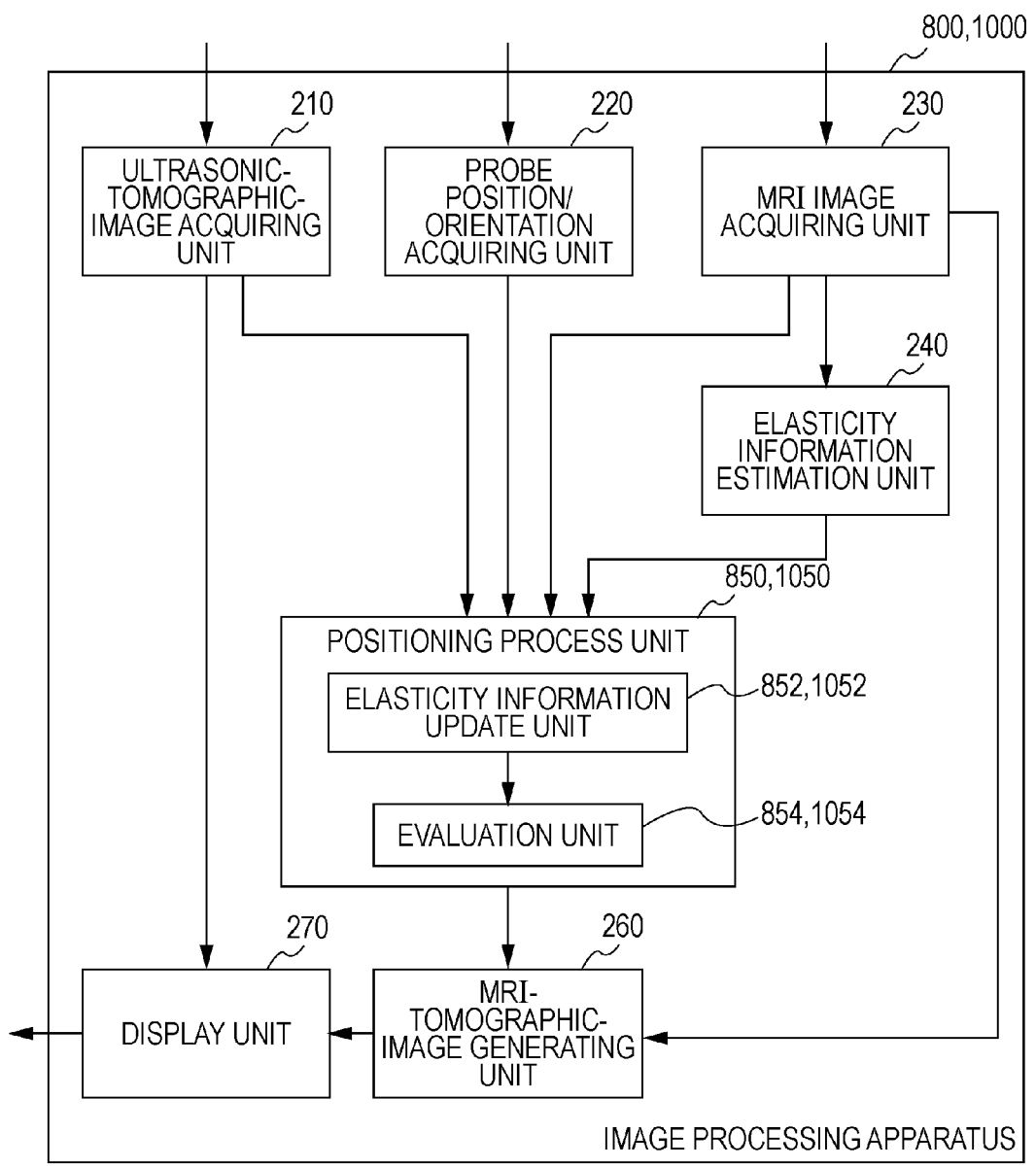
FIG. 8 is a diagram illustrating the functional structure of image processing apparatuses according to third and fourth embodiments.

FIG. 8 is a functional block diagram of the image processing apparatus 800. As shown in FIG. 8, the image processing apparatus 800 includes an ultrasonic-tomographic-image acquiring unit 210, a probe position/orientation acquiring unit 220, an MRI image acquiring unit 230, an elasticity information estimation unit 240, a positioning process unit 850, an MRI-tomographic-image generating unit 260, and a display unit 270. The functions of the above-mentioned units other than the positioning process unit 850 are similar to those in the first embodiment, and explanations thereof are thus omitted.

Similar to the positioning process unit 250 according to the first embodiment, the positioning process unit 850 performs a non-rigid body deformation positioning process for positioning the ultrasonic tomographic image acquired by the ultrasonic-tomographic-image acquiring unit 210 and the MRI image acquired by the MRI image acquiring unit 230 with respect to each other. In this process, deformation parameters of the MRI image and the position and orientation of the ultrasonic tomographic image in an MRI coordinate system are determined and are output to the MRI-tomographic-image generating unit 260. The positioning process unit 850 according to the present embodiment differs from the positioning process unit 250 according to the first embodiment in that the elasticity information regarding the MRI image input from the elasticity information estimation unit 240 is updated in the process of estimating the deformation parameters.

The positioning process unit 850 includes an elasticity information update unit 852 (second elasticity information estimation unit) which updates information (second elasticity information) regarding the elasticity of the subject in the MRI image on the basis of the assumed deformation parameters. The positioning process unit 850 also includes an evaluation unit 854 which evaluates the positioning process using the consistency of the elasticity information. The process performed by the positioning process unit 850 having the functions of the above-mentioned units will be described below with reference to the flowchart shown in FIG. 9.

The units included in the image processing apparatus 800 shown in FIG. 8 may be provided as software which realizes the functions of the units when the software is executed by a CPU of a computer. In the present embodiment, the units included in the image processing apparatus 800 are provided as software which is installed in a single computer. The basic structure of the computer which executes the software to realize the functions of the units included in the image processing apparatus 800 is similar to that shown in FIG. 3, and explanations thereof are thus omitted.

Figure 4:
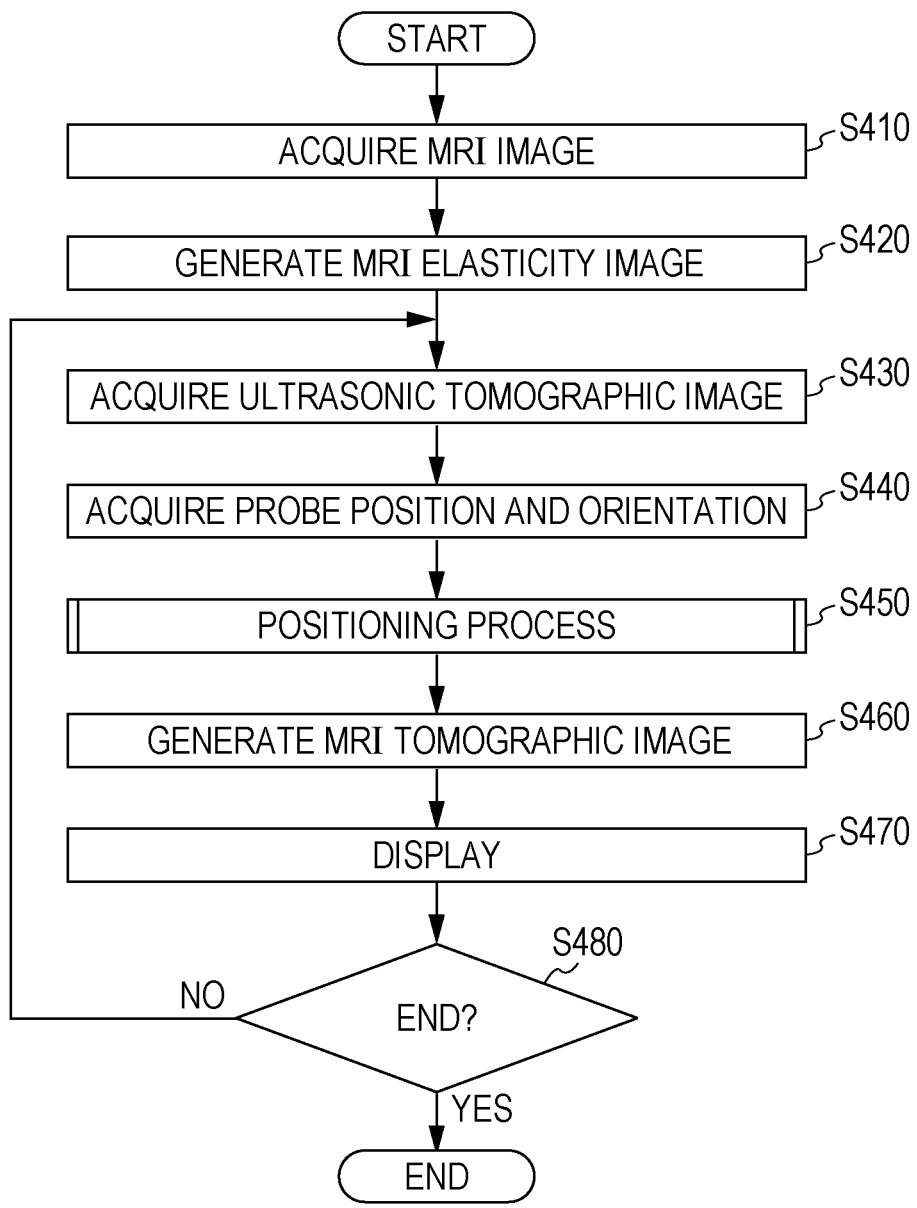
FIG. 4 is a flowchart of a process sequence performed by the image processing apparatus according to the first embodiment.

The sequence of processes performed by the image processing apparatus 800 of the present embodiment is similar to that shown in the flowchart in FIG. 4, and explanations thereof are thus omitted. In the present embodiment, the positioning process performed by the positioning process unit 850 in step S450 differs from that in the first embodiment.

Figure 9:
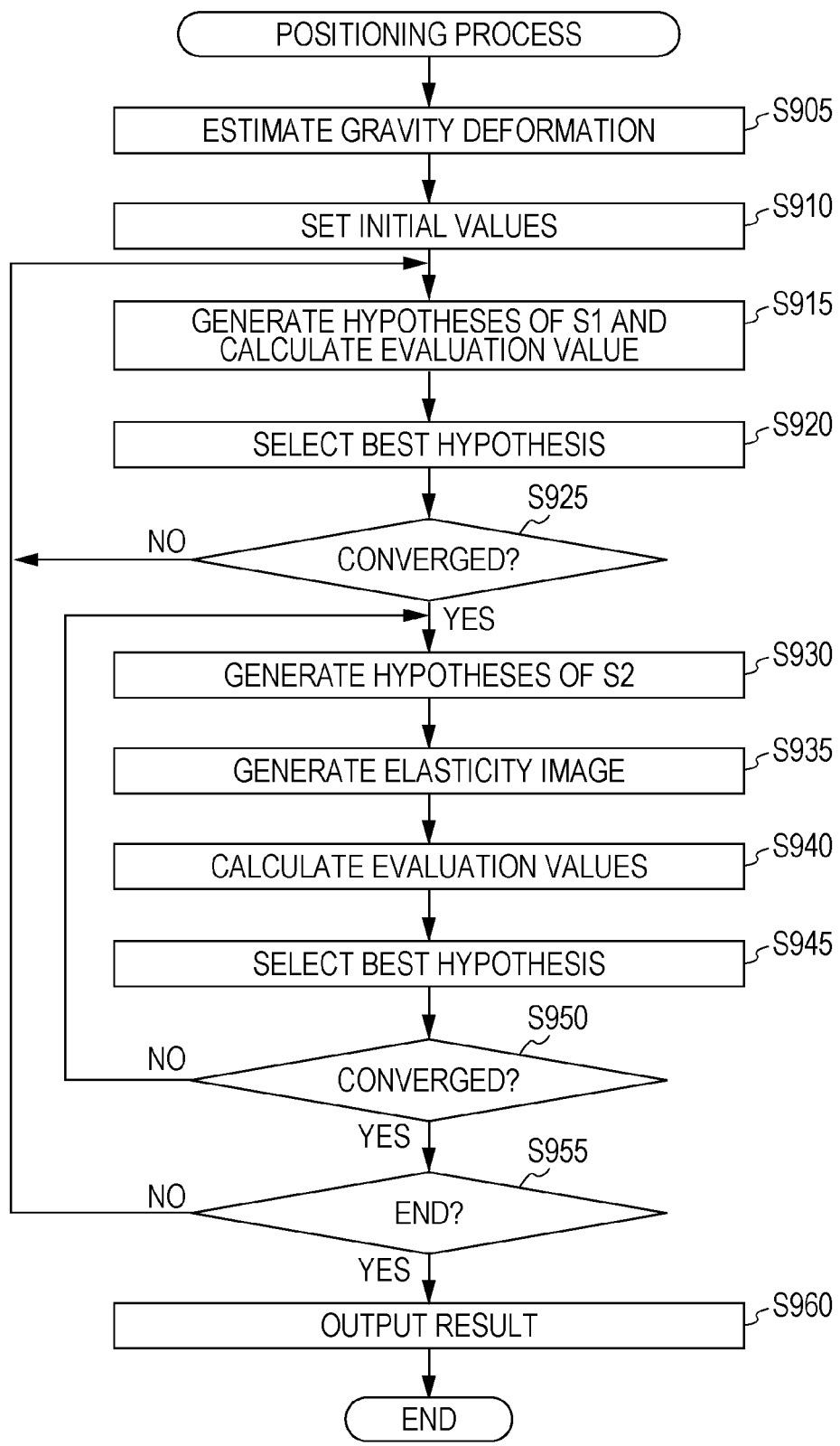
FIG. 9 is a flowchart of a process sequence performed by a positioning process unit according to the third embodiment.

The sequence of the positioning process performed by the positioning process unit 850 in step S450 will now be described with reference to the flowchart shown in FIG. 9. Similar to the above-described embodiments, in the positioning process according to the present embodiment, the position and orientation $s_1$ of the ultrasonic tomographic image in the MRI coordinate system and the deformation parameters $s_2$ of the MRI image are determined.

Step S905

In step S905, the positioning process unit 850 estimates the deformation parameters of the MRI image based on the gravity on the basis of the MRI elasticity image generated in step S420. The process performed in step S905 is similar to that performed in step S505 in the first embodiment, and detailed explanations thereof are thus omitted.

Step S910

In step S910, the positioning process unit 850 sets the unknown positioning parameters to initial values. The process performed in step S910 is similar to that performed in step S510 in the first embodiment, and detailed explanations thereof are thus omitted.

Similar to the first embodiment, in the present embodiment, the positioning process is performed by alternately estimating the parameters $s_1$ and $s_2$.

First, in steps S915 to S925, the estimated values $s_1$ of the position and orientation of the ultrasonic tomographic image are corrected to perform rigid-body positioning between the MRI image after the deformation and the ultrasonic tomographic image. The processes performed in step S915, S920, and S925 are similar to those performed in steps S525, S530, and S535, respectively, in the first embodiment, and detailed explanations thereof are thus omitted.

Next, in steps S930 to S950, the deformation parameters $s_2$ (displacements of the control points) of the MRI image are corrected to perform non-rigid-body positioning between the MRI image and the ultrasonic tomographic image.

Step S930

In step S930, the elasticity information update unit 852 generates some hypotheses about the deformation parameters by adding small different changes to the estimated values $s_2$ of the deformation parameters.

This process can be performed by calculating the positioning consistency for each of local areas near the control points in the step of evaluating the consistency for the current parameters, and then changing the displacements of the control points in accordance with the determined consistencies. More specifically, if the positioning consistency is ensured (the evaluation value is high) in a certain local area, the displacement of the control point which affects that local area is considered to be correct. Accordingly, small changes are added to only the displacements of the control points which are to be corrected. Alternatively, the amounts of small changes added to the displacements of the control points can be adjusted in accordance with the evaluation values. In such a case, combinational explosion of the hypotheses can be prevented and the process speed can be increased.

Step S935

In step S935, the elasticity information update unit 852 estimates the elasticity information of the MRI image (updates the current MRI elasticity image) on the basis of each of the deformation hypotheses generated in step S930. For example, for each control point, the average of the distances to nearby control points is calculated, and the thus-obtained value is defined as a numerical value which shows the elasticity at that point. This numerical value is the elastic modulus, which increases as the softness increases. Then, the MRI elasticity image is generated by calculating elastic moduli at coordinates other than the control points by interpolation.

Step S940

In step S940, the evaluation unit 854 evaluates the positioning consistency of the ultrasonic tomographic image positioned at $s_1$ (regarded as being fixed in this step) on the basis of each of the hypotheses generated in step S930, and calculates an evaluation value for each hypothesis. The evaluation value of the positioning consistency is calculated for each hypothesis by a method similar to that used in step S515 in the first embodiment. The present embodiment is characterized in that the image generated in step S935 for each hypothesis is used as the MRI elasticity image used for calculating the evaluation value.

Step S945

In step S945, the evaluation unit 854 selects the highest evaluation value obtained in step S940. Then, the deformation parameters of the hypothesis for which the highest evaluation value is obtained (that is, the best hypothesis) are set as the new estimated values $s_2$ of the deformation parameters. However, if the highest evaluation value is lower than the evaluation value obtained by the current estimated values, the estimated values are not updated.

Step S950

In step S950, the positioning process unit 850 determines whether or not the estimated values of the deformation parameters have converged. If it is determined that the estimated values have not yet converged, the procedure proceeds to step S930 and the process of generating some hypotheses and selecting the best hypothesis is repeated. If it is determined that the estimated values have converged, the procedure proceeds to step S955. The process performed in step S950 is similar to that performed in step S550 in the first embodiment, and detailed explanations thereof are thus omitted.

Step S955

In step S955, the positioning process unit 850 determines whether or not to repeat the above-described steps. In the case where the above-described steps are to be repeated, the procedure returns to step S915 and the current parameters are further updated. If it is not necessary to repeat the above-described steps, the procedure proceeds to step S960. The process performed in step S955 is similar to that performed in step S555 in the first embodiment, and detailed explanations thereof are thus omitted.

Step S960

In step S960, the positioning process unit 850 outputs the deformation parameters $s_2$ of the MRI image and the position and orientation $s_1$ of the ultrasonic tomographic image obtained in the above-described steps to the MRI-tomographic-image generating unit 260 as the positioning result.

The non-rigid body deformation positioning process is performed in step S450 as described above.

In the present embodiment, the elasticity image estimated by the elasticity information estimation unit 240 is used as the initial elasticity image. However, it is not necessary that this elasticity image be used as the initial elasticity image. For example, in the case where the average elastic modulus of the subject is statistically determined, the average elastic modulus may be used as the initial value. In the case where no information regarding the elasticity is obtained in advance, the process performed by the elasticity information estimation unit 240 and the process performed in step S905 may be omitted, and the following steps may be performed while the initial values (displacements of the control points) of the deformation parameters are set to 0.

By performing the above-described processes, the image processing apparatus 800 according to the present embodiment can perform high-accuracy positioning between the MRI image and the ultrasonic tomographic image by taking into consideration the consistency between the pieces of the elasticity information in the process of estimating the positioning parameters. In addition, in the present embodiment, since the elasticity image is updated in accordance with the estimation of the deformation, the accuracy of comparison between the pieces of the elasticity information can be increased.

In the methods according to the related art, it is desirable that there be no deformation between the two images which are to be positioned with respect to each other. In contrast, according to the present embodiment, the fact that there is a deformation between the two images is used. More specifically, the elasticity information derived from the deformation between the two images in the positioning process is used in the positioning process. This is the characteristics of the present embodiment.

Fourth Embodiment

An image processing apparatus according to the present embodiment has a function of acquiring both an MRI image of a subject which is captured in advance and an ultrasonic tomographic image of the subject which is being obtained by an operator (an engineer or a doctor) in an interactive manner, generating an MRI tomographic image which corresponds to the ultrasonic tomographic image, and displaying the generated MRI tomographic image.

The structure of apparatuses connected to an image processing apparatus 1000 according to the present embodiment is similar to that shown in FIG. 1. Similar to the image processing apparatus 10 according to the first embodiment, the image processing apparatus 1000 is connected to the ultrasound imaging apparatus 20, a magnetic resonance imaging apparatus 30, and a position/orientation sensor 40 via a LAN 50. These apparatuses are similar to those described in the first embodiment, and explanations thereof are thus omitted.

A functional block diagram of the image processing apparatus 1000 according to the present embodiment is similar to that shown in FIG. 8. However, the operation of the positioning process unit is different from that in the third embodiment. In the present embodiment, the positioning process unit is referred to as a positioning process unit 1050. The functions of the units other than the positioning process unit 1050 are similar to those in the third embodiment, and explanations thereof are thus omitted.

Similar to the positioning process unit 850 according to the third embodiment, the positioning process unit 1050 performs a non-rigid body deformation positioning process for positioning the ultrasonic tomographic image acquired by the ultrasonic-tomographic-image acquiring unit 210 and the MRI image acquired by the MRI image acquiring unit 230 with respect to each other. In this process, deformation parameters of the MRI image and the position and orientation of the ultrasonic tomographic image in an MRI coordinate system are determined and are output to the MRI-tomographic-image generating unit 260.

The positioning process unit 1050 includes an elasticity information update unit 1052 (second elasticity information estimation unit) which estimates deformation parameters on the basis of assumed elasticity information (second elasticity information) and an evaluation unit 1054 which evaluates the positioning process using the consistency of the elasticity information. The process performed by the positioning process unit 1050 having the functions of the above-mentioned units will be described below with reference to the flowchart shown in FIG. 10.

The units included in the image processing apparatus 1000 may be provided as software which realizes the functions of the units when the software is executed by a CPU of a computer. In the present embodiment, the units included in the image processing apparatus 1000 are provided as software which is installed in a single computer. The basic structure of the computer which executes the software to realize the functions of the units included in the image processing apparatus 1000 is similar to that shown in FIG. 3, and explanations thereof are thus omitted.

The sequence of processes performed by the image processing apparatus 1000 of the present embodiment is similar to that shown in the flowchart in FIG. 4, and explanations thereof are thus omitted. In the present embodiment, the positioning process performed by the positioning process unit 1050 in step S450 differs from those in the first and third embodiments.

Figure 10:
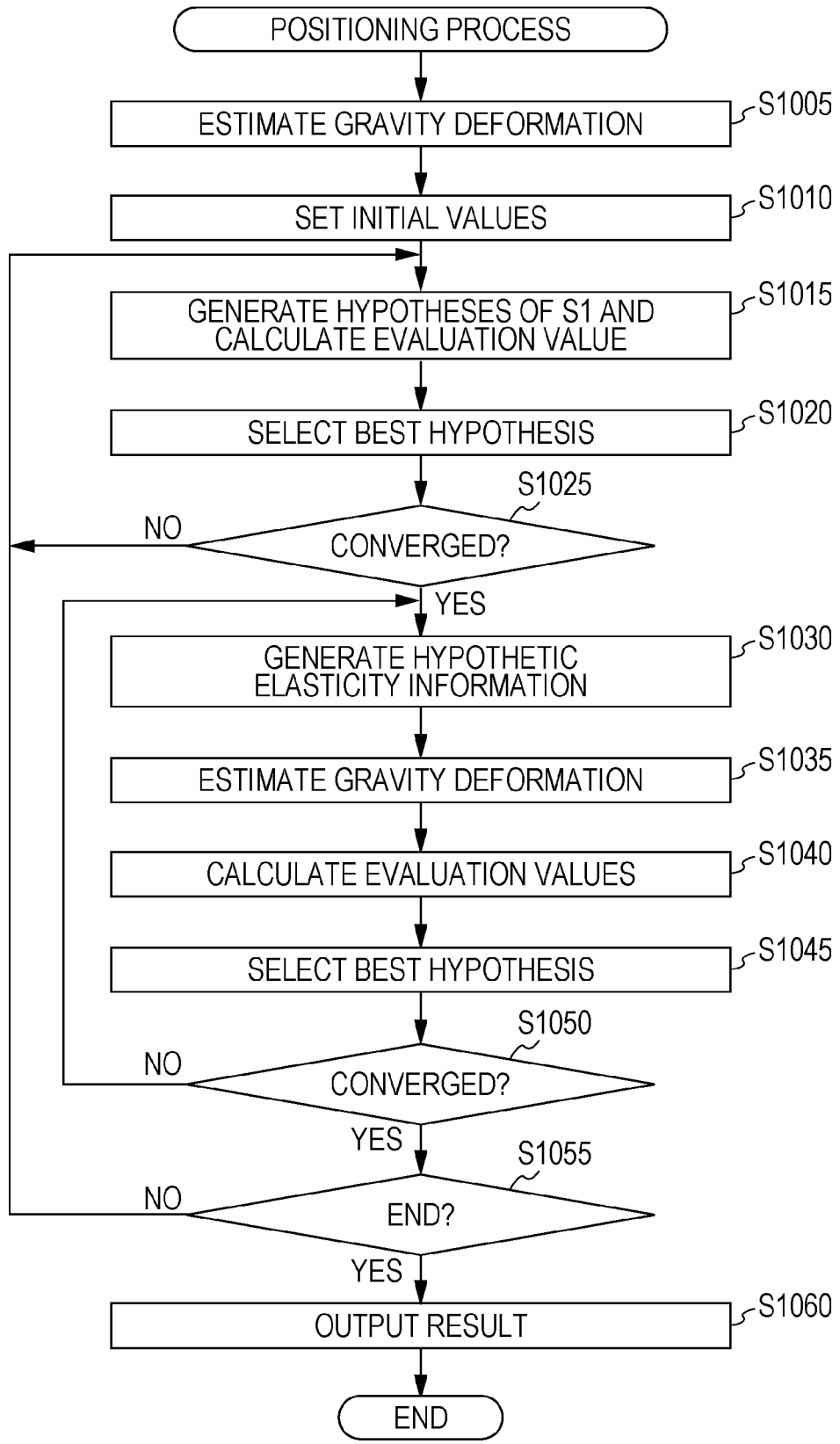
FIG. 10 is a flowchart of a process sequence performed by a positioning process unit according to the fourth embodiment.

The sequence of the positioning process performed by the positioning process unit 1050 in step S450 will now be described with reference to the flowchart shown in FIG. 10. Similar to the above-described embodiments, in the positioning process according to the present embodiment, the position and orientation $s_1$ of the ultrasonic tomographic image in the MRI coordinate system and the deformation parameters $s_2$ of the MRI image are determined.

Step S1005

In step S1005, the positioning process unit 1050 estimates the deformation parameters of the MRI image based on the gravity on the basis of the MRI elasticity image generated in step S420. The process performed in step S1005 is similar to that performed in step S505 in the first embodiment, and detailed explanations thereof are thus omitted.

Step S1010

In step S1010, the positioning process unit 1050 sets the unknown positioning parameters to initial values. The process performed in step S1010 is similar to that performed in step S510 in the first embodiment, and detailed explanations thereof are thus omitted.

Also in the present embodiment, the positioning process is performed by alternately estimating the parameters $s_1$ and $s_2$.

First, in steps S1015 to S1025, the estimated values $s_1$ of the position and orientation of the ultrasonic tomographic image are corrected to perform rigid-body positioning between the MRI image after the deformation and the ultrasonic tomographic image. The processes performed in step S1015, S1020, and S1025 are similar to those performed in steps S525, S530, and S535, respectively, in the first embodiment, and explanations thereof are thus omitted.

Next, insteps S1030 to S1050, the deformation parameters $s_2$ (displacements of the control points) of the MRI image are corrected to perform non-rigid-body positioning between the MRI image and the ultrasonic tomographic image.

Step S1030

In step S1030, the elasticity information update unit 1052 generates some hypotheses about the correction of the current MRI elasticity image. More specifically, small changes are added to the elastic moduli for the control points set in the elasticity image. Then, the elastic moduli for the entire area of the image are obtained by interpolation.

This process can be performed by calculating the positioning consistency for each of local areas near the control points in the step of evaluating the consistency for the current parameters, and then changing the amount of changes for the control points in accordance with the determined consistencies. More specifically, if the positioning consistency is ensured (the evaluation value is high) in a certain local area, the elastic modulus for the control point which affects that local area is considered to be correct. Accordingly, new hypotheses are generated only for the elastic moduli for the control points which are to be corrected. Alternatively, the amounts of changes added to generate the hypotheses can be adjusted in accordance with the evaluation values. In such a case, combinational explosion of the hypotheses can be prevented and the process speed can be increased.

Step S1035

In step S1035, the elasticity information update unit 1052 estimates the deformation parameters due to the gravity by a process similar to that performed in step S1005 on the basis of each of the hypotheses generated in step S1030. The thus-estimated deformation parameters are defined as a group of candidates of deformation parameters $s_2$.

Step S1040

In step S1040, the evaluation unit 1054 evaluates the positioning consistency of the ultrasonic tomographic image positioned at $s_1$ (regarded as being fixed in this step) on the basis of the group of candidates of the deformation parameters generated in step S1035, and calculates an evaluation value for each hypothesis. The evaluation value of the positioning consistency is calculated for each hypothesis by a method similar to that used in step S515 in the first embodiment. The present embodiment is characterized in that each of the hypotheses generated in step S1030 is used as the MRI elasticity image for calculating the evaluation value.

Step S1045

In step S1045, the evaluation unit 1054 selects the highest evaluation value obtained in step S1040. Then, the candidates of the deformation parameters $s_2$ corresponding to the highest evaluation value are set as the new estimated values $s_2$ of the deformation parameters. However, if the highest evaluation value is lower than the evaluation value obtained by the current estimated values, the estimated values are not updated.

Step S1050

In step S1050, the positioning process unit 1050 determines whether or not the estimated values of the deformation parameters have converged. If it is determined that the estimated values have not yet converged, the procedure proceeds to step S1030 and the process of generating some hypotheses and selecting the best hypothesis is repeated. If it is determined that the estimated values have converged, the procedure proceeds to step S1055. The process performed in step S1050 is similar to that performed in step S550 in the first embodiment, and detailed explanations thereof are thus omitted.

Step S1055

In step S1055, the positioning process unit 1050 determines whether or not to repeat the above-described steps. In the case where the above-described steps are to be repeated, the procedure returns to step S1015 and the current parameters are further updated. If it is not necessary to repeat the above-described steps, the procedure proceeds to step S1060. The process performed in step S1055 is similar to that performed in step S555 in the first embodiment, and detailed explanations thereof are thus omitted.

Step S1060

In step S1060, the positioning process unit 1050 outputs the deformation parameters $s_2$ of the MRI image and the position and orientation $s_1$ of the ultrasonic tomographic image obtained in the above-described steps to the MRI-tomographic-image generating unit 260 as the positioning result.

The non-rigid body deformation positioning process is performed in step S450 as described above.

In the present embodiment, the elasticity image estimated by the elasticity information estimation unit 240 is used as the initial elasticity image. However, it is not necessary that this elasticity image be used as the initial elasticity image. For example, in the case where the average elastic modulus of the subject is statistically determined, the average elastic modulus may be used as the initial value. In the case where no information regarding the elasticity is obtained in advance, the process performed by the elasticity information estimation unit 240 and the process performed in step S1005 may be omitted, and the following steps may be performed while the initial values (displacements of the control points) of the deformation parameters are set to 0.

In addition, in the present embodiment, only the deformation based on the gravity is taken into consideration. However, in the case where the actual deformation is caused not only by the gravity but also by other factors, deformation other than the deformation caused by the gravity may also be taken into consideration. For example, processes corresponding to those performed in steps S540 and S545 in the first embodiment may be performed after the process of step S1045. Accordingly, the deformation parameters which cannot be expressed on the basis of the deformation due to the gravity can be estimated.

Also in the present embodiment, effects similar to those obtained by the third embodiment can be obtained.

First Modification

Figure 5:
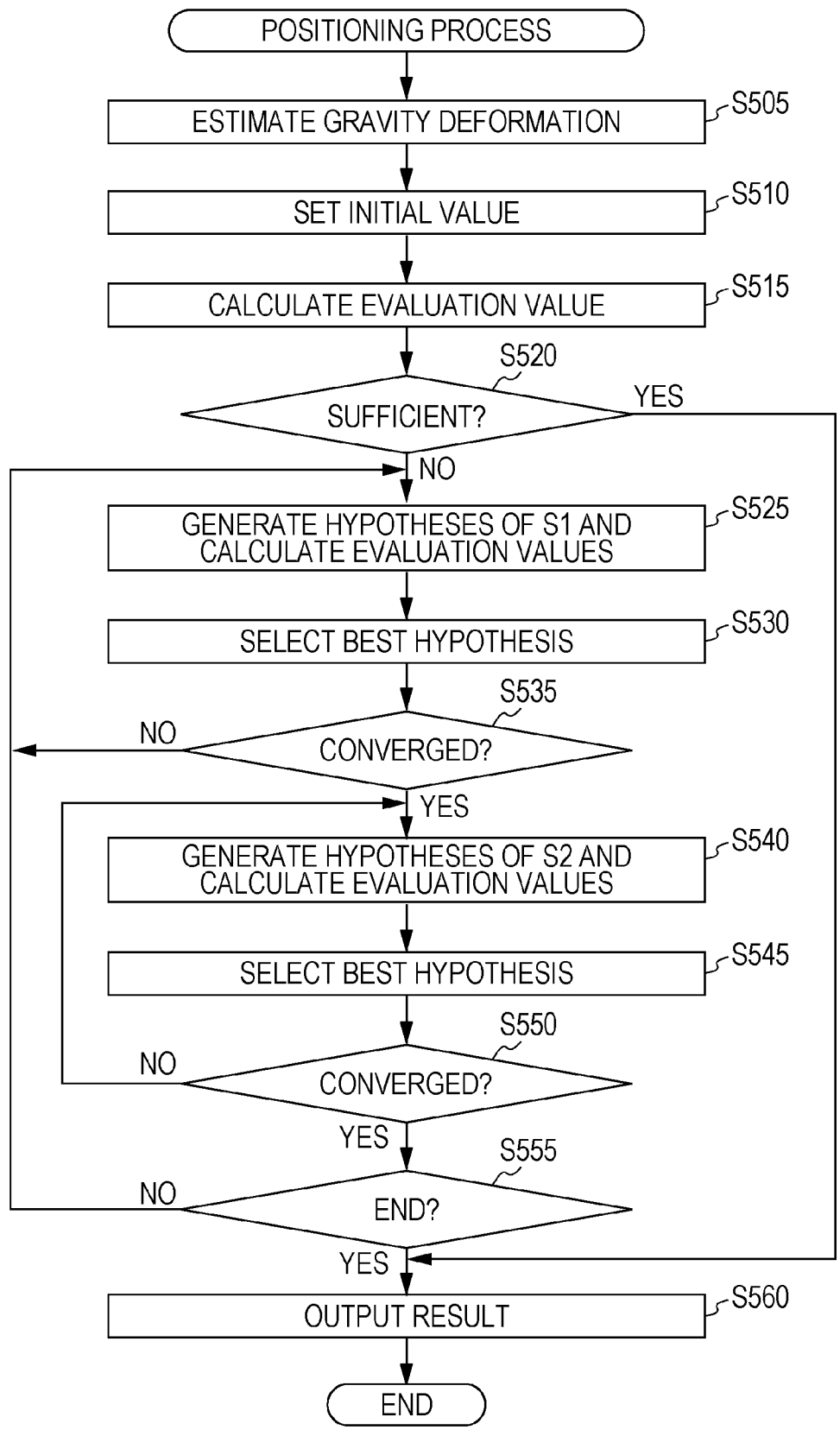
FIG. 5 is a flowchart of a process sequence performed by a positioning process unit according to the first embodiment.

In the first and second embodiments, the non-rigid body deformation positioning process is performed in accordance with the flowchart shown in FIG. 5. However, the sequence of the process performed by the positioning process unit 250 (650) is not limited to that in the flowchart. This also applies to the third and fourth embodiments.

For example, if it can be assumed that the deformation is caused only by the gravity, the direction of gravity with respect to the subject in the MRI process and the direction of gravity with respect to the subject in the ultrasound imaging process can be estimated as the deformation parameters e2. The directions of gravity provided as the known values can be used as the initial values of $s_2$. Then, in steps S540 to S550 regarding the non-rigid body deformation positioning process, step S540 can be changed as follows. That is, first, some hypotheses are generated by adding small different changes to current $s_2$ (estimated values of the directions of gravity). Then, for each hypothesis, the displacements of the control points are estimated by a process similar to the process performed in step S505. Then, the positioning consistency between the MRI image deformed on the basis of the estimated displacements and the ultrasonic tomographic image positioned at $s_1$ (regarded as being fixed in this step) is evaluated, and an evaluation value is calculated. Then, the selection of the best hypothesis (S545) and the determination of convergence (S550) can be performed in the above-described manner.

Two types of deformation parameters, i.e., the directions of gravity and the displacements of the control points which cannot be expressed by the directions of gravity, can both be estimated. In such a case, the above-described process of estimating the directions of gravity can be added between steps S535 and S540.

In the case where the posture of the subject can be accurately controlled, the procedure can also be such that estimation of the deformation parameters is performed only in step S505 and only the rigid body positioning process is performed after step S505 (in other words, the processes in steps S540 to S550 are omitted). In addition, in the case where the deformation of the subject due to the gravity is small, the process of step S505 can be omitted. In addition, in the case where the deformation of the subject is sufficiently small, it can be assumed that the subject is a rigid body and the processes of steps S505 and S540 to S550 can be omitted. In this case, only the rigid-body positioning process is performed as the positioning process. In other words, the estimated parameters are only the position and orientation of the ultrasonic tomographic image in the MRI coordinate system.

The above-described approach of determining the evaluation value for each of the generated hypotheses and selecting the best hypothesis may be replaced by another method. For example, the positioning process may also be performed by the following method. First, the ultrasonic tomographic image (the ultrasonic elasticity image) is divided into a plurality of blocks. Next, the consistency between each block and each of portions of MRI image (the MRI elasticity image) extracted from a search area set near the area corresponding to the block is evaluated. Then, the position (corresponding point) of the portion of the MRI image (the MRI elasticity image) which provides the highest consistency is selected for each block. Then, the position and orientation of the ultrasonic tomographic image are updated on the basis of the group of corresponding points obtained as described above. The consistency evaluation is performed on the basis of the consistency between the MRI elasticity image and the ultrasonic elasticity image and the consistency between the MRI image and the ultrasonic tomographic image.

The sequence of the processes performed by the positioning process unit 250 is not limited to the above-described sequence, and any method can be used as long as the consistency between the pieces of elasticity information obtained by different modalities is taken into consideration in the process of estimating the positioning parameters.

Second Modification

In the first, third, and fourth embodiments, the elasticity information estimation unit 240 estimates the tissue structure from the MRI image, and the elasticity information of the MRI image is estimated on the basis of the tissue structure. In the second embodiment, the elasticity information of the subject in the MRI image is estimated using a plurality of MRI images obtained while the subject is in different postures. However, the method for obtaining the elasticity information is not limited to this, and the elasticity information may also be obtained by other methods. For example, the elasticity information can be estimated on the basis of the tissue structure extracted from an MRI image captured while the subject is in a certain posture, and the thus-obtained elasticity information can be used in the positioning process for positioning the MRI image and an MRI image obtained while the subject is in another posture with respect to each other. Then, the estimation of the elasticity information can be performed again on the basis of the result of the positioning process. In the case where the magnetic resonance imaging apparatus 30 has a function of generating the MRI elasticity image, the image processing apparatus 10 can also receive the MRI elasticity image from the magnetic resonance imaging apparatus 30.

Third Modification

In the above-described embodiments, an MRI tomographic image corresponding to the ultrasonic tomographic image is generated using the result of the positioning process, and the thus-obtained MRI tomographic image is displayed next to the ultrasonic tomographic image. However, it is not always necessary to perform this process. For example, the generated MRI tomographic image can be recorded in the external storage device 304. Alternatively, the generated MRI tomographic image can be output to an external device through the interface 308. Alternatively, the generated MRI tomographic image and the ultrasonic tomographic image may be displayed such that they are superimposed on each other.

Instead of generating the MRI tomographic image, a three-dimensional position of a region of interest (for example, a tumor), which is identified on the MRI image, can be determined, and the position of the region of interest on the ultrasonic tomographic image can be determined by using the result of the positioning process. In addition, an application for superimposing the obtained information on the ultrasonic tomographic image may be provided. In addition, the deformation parameters of the MRI image and the position and orientation of the ultrasonic tomographic image, that is, the result of the positioning process, may be stored in the RAM 302 or the external storage device 304 such that the result of the positioning process can be used by another application. The result of the positioning process can also be output to an external device through the interface 308.

Fourth Modification

In the above-described embodiments, the MRI apparatus is explained as the second modality for acquiring a three-dimensional medical image. However, the second modality is not limited to this. For example, another modality, such as an X-ray CT apparatus, a SPECT apparatus, or a PET apparatus, which generates three-dimensional medical images, may also be used as the second modality. Similarly, the first modality is not limited to the ultrasound imaging apparatus. For example, a photo-acoustic tomography (PAT) apparatus which obtains an image of a subject using a laser source and a probe including ultrasound probe elements may also be used. It is not necessary that the first modality and the second modality be different modalities, and images obtained by the same modality under different conditions can also be subjected to the positioning process. For example, images obtained by different apparatuses of the same modality (for example, apparatuses produced by different manufacturers) or images obtained by the same apparatus under different conditions can also be subjected to the positioning process.

Other Embodiments

The present invention can also be carried out by supplying a recording medium (or a storage medium), in which a software program code which realizes the functions of the above-described embodiment is stored, to a system or an apparatus, and causing a computer (CPU or MPU) of the system or the apparatus to read and execute the program code stored in the recording medium. In this case, the program code read from the recording medium itself realizes the functions of the above-described embodiments, and the recording medium that stores the program code constitute the present invention.

In addition to the execution of the program code read by the computer, the functions of the above-described embodiments can, of course, also be realized by causing an operating system (OS) that operates on the computer to perform some or all of the actual processes in response to instructions of the program code.

The functions of the above-described embodiments can, of course, also be realized by storing the program code read from the recording medium in a memory of a function extension card inserted in the computer or a function extension unit connected to the computer, and causing a CPU included in the function extension card or the function extension unit to perform some or all of the actual processes in response to instructions of the program code.

In the case where the present invention is applied to a recording medium as described above, the program code corresponding to the above-described flowcharts is stored in the recording medium.

The descriptions of the embodiments illustrate examples of the image processing apparatus according to the present invention, and the present invention is not limited to the above-described embodiments.

As many apparently widely different embodiments of the present invention can be made without departing from the spirit and scope thereof, it is to be understood that the invention is not limited to the specific embodiments thereof except as defined in the claims.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2008-296698, filed Nov. 20, 2008, which is hereby incorporated by reference herein in its entirety.

The invention claimed is:

1. An image processing apparatus which positions a first image of a subject and a second image of the subject, the image processing apparatus comprising:
- a first elasticity information acquiring unit configured to acquire first elasticity information regarding elasticity of the subject in the first image obtained using a first imaging apparatus;
- a second elasticity information acquiring unit configured to acquire second elasticity information regarding the elasticity of the subject in the second image obtained using a second imaging apparatus;
- an evaluating unit configured to evaluate consistency between the first elasticity information in the first image and the second elasticity information in the second image; and
- a registration unit configured to register the first image and the second image with respect to each other on the basis of the consistency between the first elasticity information in the first image and the second elasticity information in the second image.

2. The image processing apparatus according to claim 1, wherein the registration unit deforms the second image in accordance with the gravity on the basis of the second elasticity information.

3. The image processing apparatus according to claim 1, wherein the second elasticity information acquiring unit estimates information regarding the elasticity of the subject as the second elasticity information on the basis of a distance between corresponding pixels in a plurality of images captured while the subject is in a plurality of postures.

4. The image processing apparatus according to claim 1, wherein the registration unit deforms at least one of the first image and the second image based on a value calculated by the evaluating unit.

5. The image processing apparatus according to claim 4, wherein the evaluating unit evaluates the consistency between the first image and the second image in addition to the consistency between the first elasticity information and the second elasticity information, and changes a ratio of evaluation between the consistency between the first elasticity information and the second elasticity information and the consistency between the first image and the second image on the basis of elasticity information of the subject.

6. The image processing apparatus according to claim 4, wherein the evaluating unit evaluates the consistency between the first image and the second image in addition to the consistency between the first elasticity information and the second elasticity information, and changes a ratio of evaluation between the consistency between the first elasticity information and the second elasticity information and the consistency between the first image and the second image on the basis of a posture of the subject in an image capturing process.

7. The image processing apparatus according to claim 1, wherein the first image is captured by an ultrasound imaging apparatus.

8. The image processing apparatus according to claim 1, wherein the second image is captured by a magnetic resonance imaging apparatus.

9. An image processing method for registering a first image of a subject and a second image of the subject, the image processing method comprising:
- acquiring first elasticity information regarding elasticity of a subject in the first image obtained using a first imaging apparatus;
- acquiring second elasticity information regarding the elasticity of the subject in the second image obtained using a second imaging apparatus;
- evaluating consistency between the first elasticity information in the first image and the second elasticity information in the second image; and
- registering the first image and the second image with respect to each other on the basis of the consistency between the first elasticity information in the first image and the second elasticity information in the second image.

10. A computer-readable storage medium which stores a program for allowing a computer to execute the image processing method according to claim 9.

11. The image processing apparatus according to claim 1, wherein the registering unit deforms at least one of the first image and the second image based on a registration consistency between the first elasticity information and the second elasticity information.

12. The image processing apparatus according to claim 1, wherein at least one of the first elasticity information and the second elasticity information is information about elasticity parameters stored beforehand for each tissue of a corresponding image being substituted into each tissue.

13. The image processing apparatus according to claim 1, wherein the image is one of an ultrasonic-tomographic-image and an MRI image.

14. An image processing apparatus which positions a first image and a second image of the subject, the image processing apparatus comprising:
- an acquiring unit configured to acquire first elasticity information corresponding to the first image obtained using a first imaging apparatus and to acquire second elasticity information corresponding to the second image obtained using a second imaging apparatus;
- an evaluating unit configured to evaluate consistency between the first elasticity information in the first image and the second elasticity information in the second image; and
- a deforming unit configured to deform the first image so as to be consistent with the second image based on the consistency between the first elasticity information in the first image and the second elasticity information in the second image.

15. An image processing method of positioning a first image and a second image of a subject, comprising:
- acquiring first elasticity information corresponding to the first image obtained using a first imaging apparatus;
- acquiring second elasticity information corresponding to the second image obtained using a second imaging apparatus;
- evaluating consistency between the first elasticity information in the first image and the second elasticity information in the second image; and
- deforming the first image so as to be consistent with the second image based on the consistency between the first elasticity information in the first image and the second elasticity information in the second image.

16. An image processing apparatus which positions a first image and a second image of the subject, the image processing apparatus comprising:
- an acquiring unit configured to acquire first elasticity information corresponding to the first image obtained using a first imaging apparatus and second elasticity information corresponding to the second image obtained using a second imaging apparatus;

an evaluating unit configured to evaluate consistency between the first elasticity information in the first image and the second elasticity information in the second image; and a registration unit configured to register the first image and the second image based on consistency information to make the first elasticity information in the first image and the second elasticity information in the second image consistent with each other.

17. The image processing apparatus according to claim 16, wherein the registration unit deforms at least one of the first image and the second image based on a registration consistency between the first information and the second information.

18. The image processing apparatus according to claim 1, wherein the second elasticity information acquiring unit acquires the second elasticity information in the second image using images obtained while the subject is in different postures.

19. The image processing apparatus according to claim 1, wherein the second elasticity information acquiring unit acquires the second elasticity information in the second image using statistics of a tissue structure estimated from the second image.

* * * * *